(12) United States Patent
Hwa et al.

(10) Patent No.: US 9,132,191 B2
(45) Date of Patent: Sep. 15, 2015

(54) COMPOSITIONS AND METHODS OF PREVENTING OR AMELIORATING ABNORMAL THROMBUS FORMATION AND CARDIOVASCULAR DISEASE

(75) Inventors: John Hwa, Madison, CT (US); WaiHo Tang, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/123,879

(22) PCT Filed: Jun. 5, 2012

(86) PCT No.: PCT/US2012/040887
§ 371 (c)(1),
(2), (4) Date: Jan. 14, 2014

(87) PCT Pub. No.: WO2012/170405
PCT Pub. Date: Dec. 13, 2012

(65) Prior Publication Data
US 2014/0147448 A1 May 29, 2014

Related U.S. Application Data

(60) Provisional application No. 61/494,657, filed on Jun. 8, 2011.

(51) Int. Cl.
| | |
|---|---|
| *A61K 39/395* | (2006.01) |
| *A61K 31/425* | (2006.01) |
| *A61K 31/499* | (2006.01) |
| *A61K 31/195* | (2006.01) |
| *A61K 31/353* | (2006.01) |
| *C12N 15/113* | (2010.01) |
| *A61K 31/197* | (2006.01) |
| *A61K 31/4162* | (2006.01) |
| *A61K 31/426* | (2006.01) |
| *A61K 31/428* | (2006.01) |
| *A61K 31/4747* | (2006.01) |
| *A61K 31/502* | (2006.01) |
| *A61K 31/517* | (2006.01) |
| *A61K 31/616* | (2006.01) |
| *A61K 31/713* | (2006.01) |

(52) U.S. Cl.
CPC .......... *A61K 39/3955* (2013.01); *A61K 31/195* (2013.01); *A61K 31/197* (2013.01); *A61K 31/353* (2013.01); *A61K 31/4162* (2013.01); *A61K 31/425* (2013.01); *A61K 31/426* (2013.01); *A61K 31/428* (2013.01); *A61K 31/4747* (2013.01); *A61K 31/499* (2013.01); *A61K 31/502* (2013.01); *A61K 31/517* (2013.01); *A61K 31/616* (2013.01); *A61K 31/713* (2013.01); *C12N 15/1137* (2013.01); *C12Y 101/01021* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2006/0293265 A1 | 12/2006 | Srivastava et al. | |
| 2008/0031964 A1* | 2/2008 | Messadek | 424/490 |
| 2009/0082256 A1* | 3/2009 | Abe et al. | 514/4 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Guido et al (Curr Med Chem. 2008;15(1):37-46).*
Clark et al (J. Med. Chem., 2014, 57 (12), pp. 5023-5038).*
Aagaard et al (Advanced Drug Delivery Reviews 59 (2007) 75-86).*
Warzocha et al (Leukemia and Lymphoma, Val. 24 (1997) pp. 267-281).*
International Search Report mailed Sep. 25, 2012; PCT Application No. PCT/US2012/040887.
Mason, at al., "Aspirin Resistance and Atherothrombotic Disease", Journal of the American College of Cardiology; 2005; vol. 46, No. 6, pp. 986-993.
Tang at al., "Glucose and collagen reaulate human platelet activity through aldose reductase inducton of thromboxane", The Journal of Clinical Investivation, Nov. 2011, vol. 121, No. 11, pp. 4462-4476.
Vikramadithyan et al., "Human aldose reductase expression accelerates diabetic atherosclerosis in transgenic mice", The Journal of Clinical Investigation, 2005, vol. 115, No. 9, pp. 2434-2443.

* cited by examiner

*Primary Examiner* — Brian J Gangle
*Assistant Examiner* — Andrea McCollum
(74) *Attorney, Agent, or Firm* — Saul Ewing LLP; Kathryn Doyle; Domingos J. Silva

(57) ABSTRACT

The invention includes compositions and methods useful for treating preventing abnormal thrombus formation and subsequent cardiovascular disease in diabetic patients and patients with increased cardiovascular risk.

11 Claims, 32 Drawing Sheets

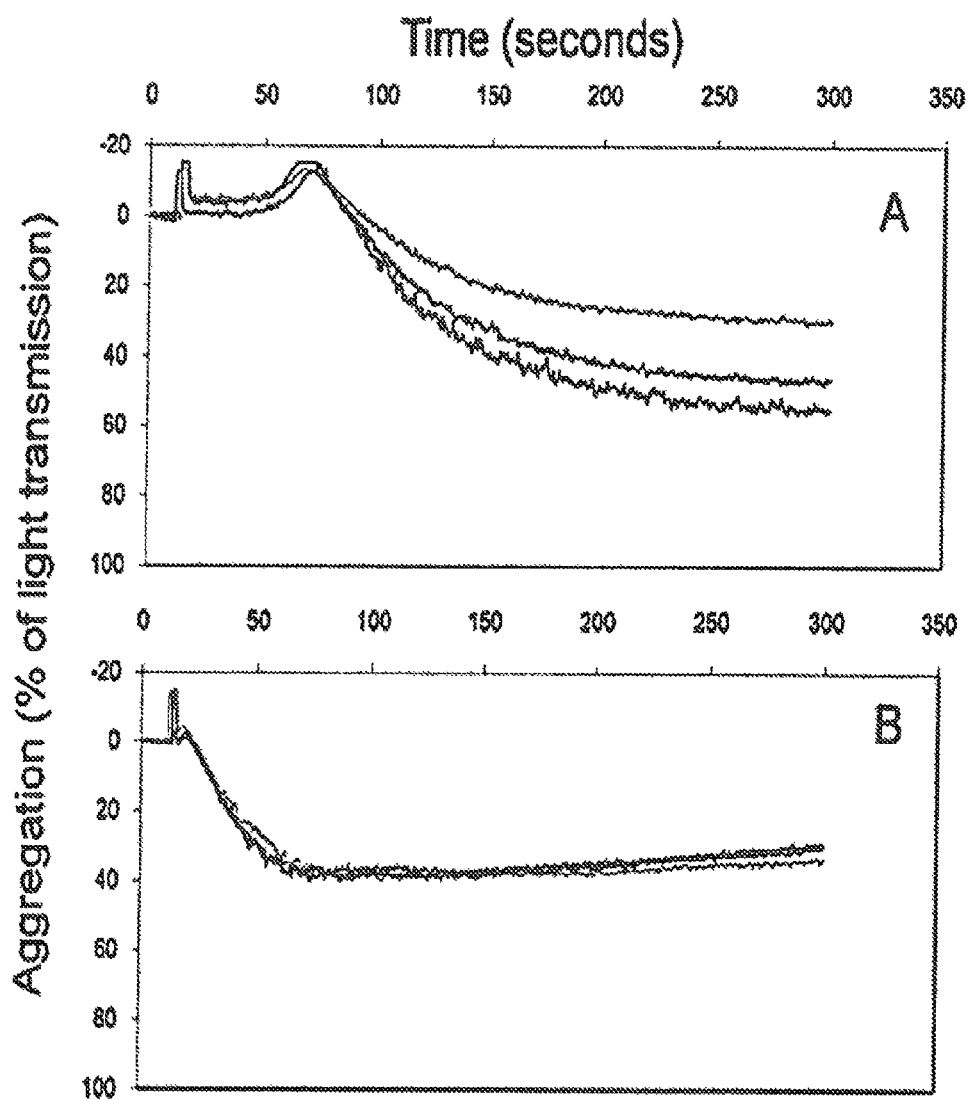

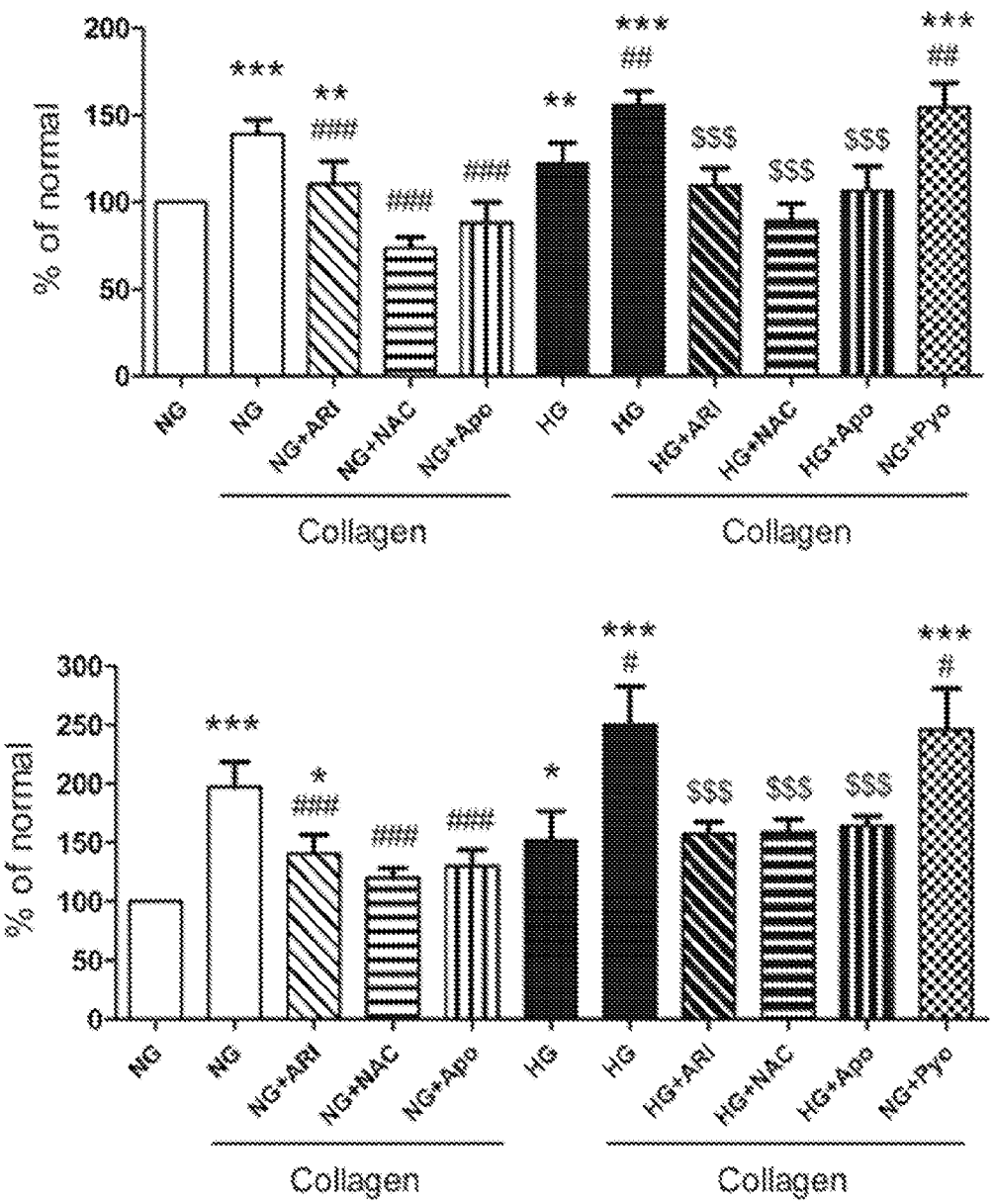

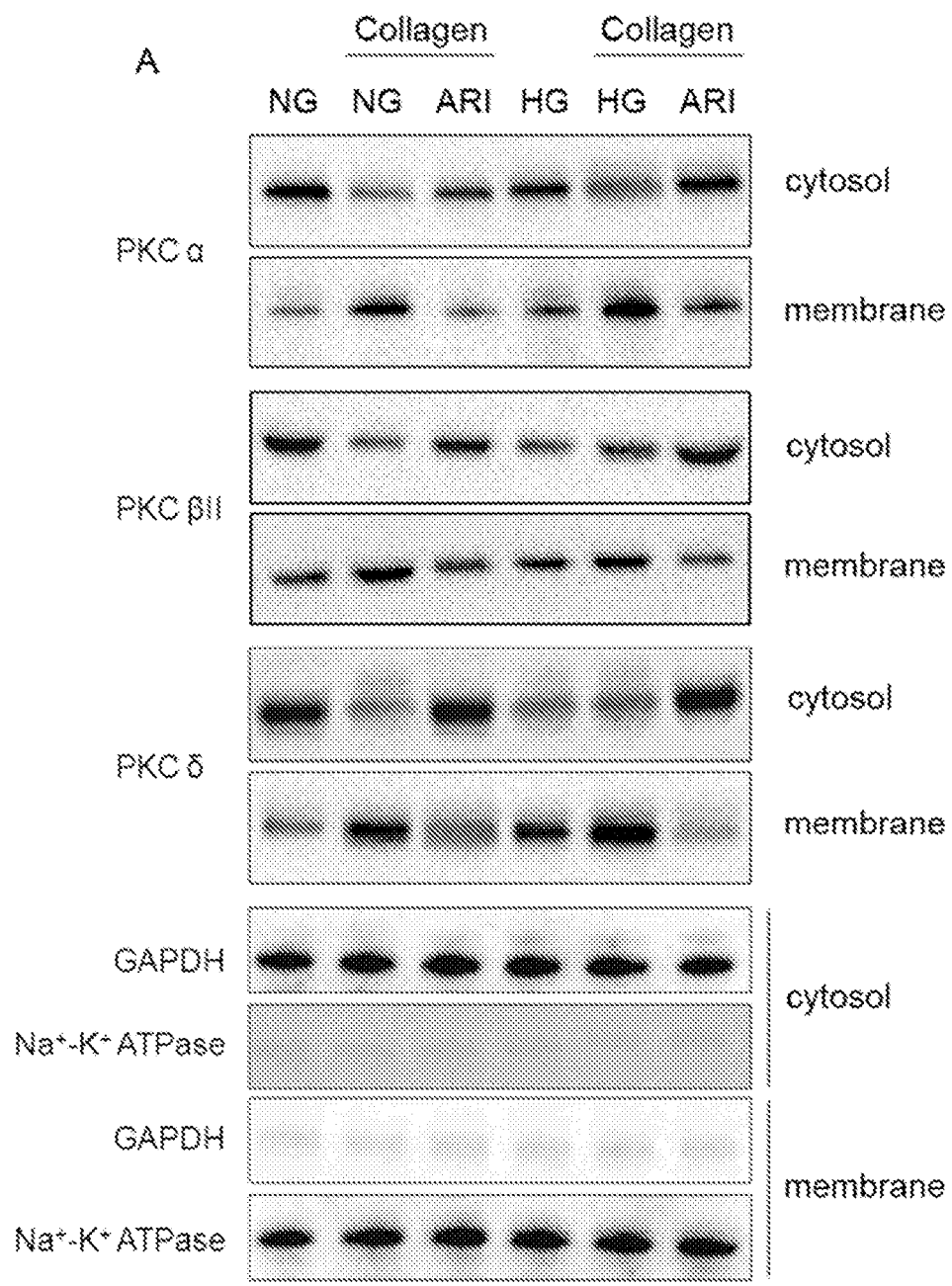

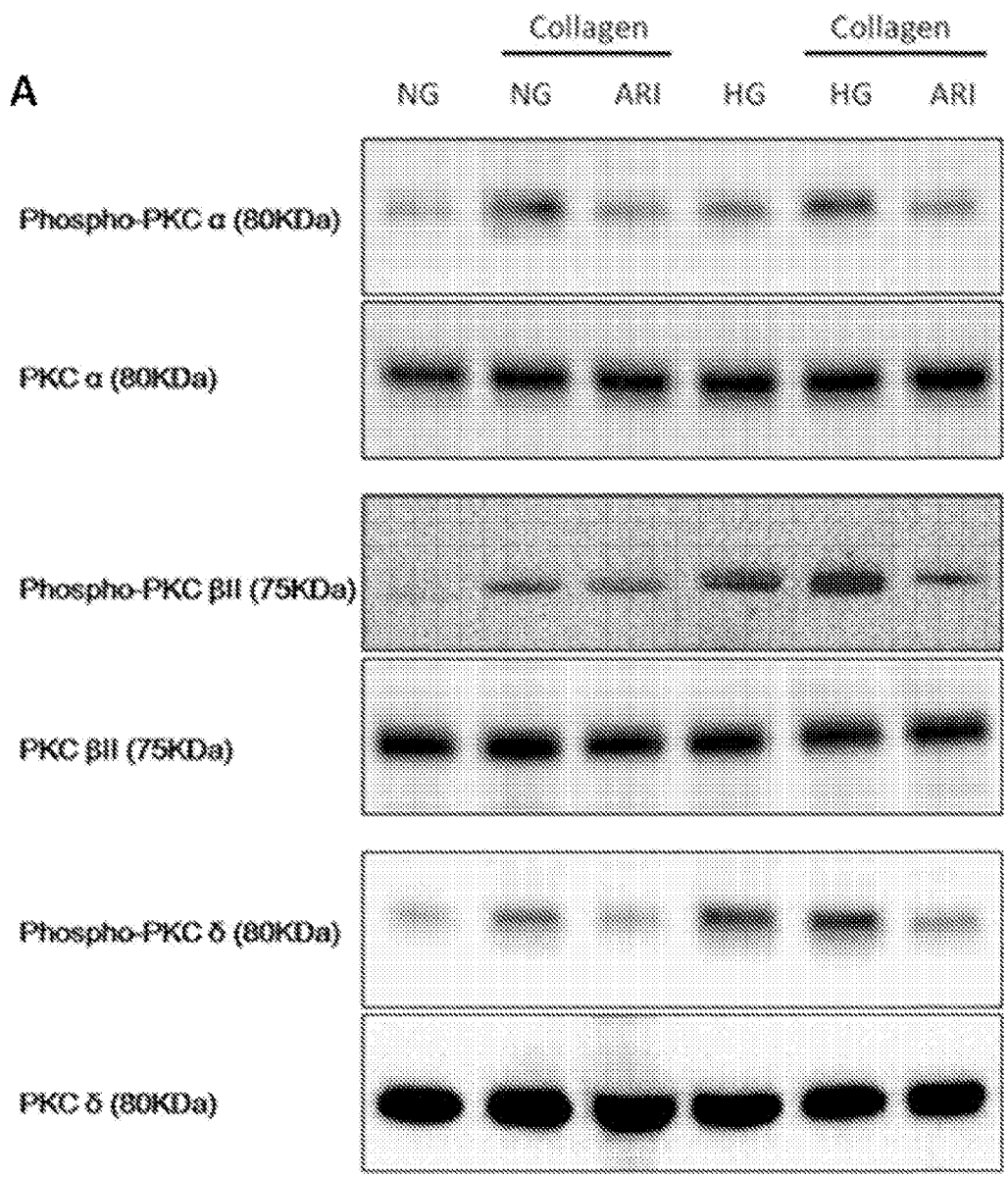

COMPOSITIONS AND METHODS OF PREVENTING OR AMELIORATING ABNORMAL THROMBUS FORMATION AND CARDIOVASCULAR DISEASE

CROSS-REFERENCE TO RELATED APPLICATIONS

This application is the U.S. national phase application filed under 35 U.S.C. §371 and claiming priority to International Patent Application No. PCT/US2012/040887, filed Jun. 5, 2012, which is entitled to priority under 35 U.S.C. §119(e) to U.S. Provisional Patent Application No. 61/494,657, filed Jun. 8, 2011, all of which are hereby incorporated by reference in their entireties.

BACKGROUND OF THE INVENTION

Accelerated atherosclerosis and microvascular disease contribute to the morbidity and mortality associated with diabetes mellitus (Beckman et al., 2002, JAMA 287:2570-2581; D'Souza et al., 2009, Mol. Cell. Biochem. 331:89-116; Kannel & McGee, 1979, JAMA 241:2035-2038). Vascular inflammation, endothelial dysfunction associated with hyperglycemia, impaired fibrinolysis and increased coagulation factors, as well as abnormal platelet function, are typical for diabetes, contributing to the increased thrombotic events and development of arteriosclerosis (Carr, 2001, J. Diabetes Complications 15:44-54). Altered platelet function in diabetes mellitus (DM), including altered adhesion and aggregation, may participate in the pathogenesis of diabetic vascular complications by promoting microthrombus formation (Bern, 1978, Diabetes 27:342-350; Brownlee, 2001, Nature 414:813-820; Gugliucci, 2000, J. Am. Osteopath. Assoc. 100:621-634; Wautier & Guillausseau, 1998, Vasc. Med. 3:131-137), contributing to enhanced risk of small vessel occlusions and accelerated atherothrombotic diseases (Carr, 2001, J. Diabetes Complications 15:44-54; Calles-Escandon et al., 1999, Coron. Artery Dis. 10:23-30; De Cristofaro et al., 2003, J. Thromb. Haemost. 1:250-256). Patients with Type 2 (T2) DM exhibit platelet hyper-reactivity both in vitro and in vivo, coupled with biochemical evidence of persistently increased thromboxane (TX)-dependent platelet activation (Davi et al., 1990, N. Engl. J. Med. 322:1769-1774; Ferroni et al., 2004, J. Thromb. Haemost. 2:1282-1291; Watala et al., 2005, Pharmacol. Rep. 57 Suppl:42-5). The mechanism by which platelets transduce glucose levels into enhanced TX generation independent of endothelial and other blood cell derived factors remains unclear. Similarly, optimal antiplatelet therapy for diabetic patients remains to be achieved.

Aldose reductase (AR) is the first enzyme of the polyol pathway, and it represents a minor source of glucose utilization, accounting for less than 3% of glucose consumption under euglycemia. However, under hyperglycemia, the activity of AR is substantially increased, representing up to 30% of total glucose consumption, and the abnormal activation of the polyol pathway leads to depletion of reducing equivalents and accumulation of osmotically active polyols (Bhatnagar & Srivastava, 1992, Biochem. Med. Metab. Biol. 48:91-121). Therefore, enhanced utilization of this pathway is well known to contribute to microvascular and macrovascular diabetic complications by increasing the oxidative and osmotic stress. Also, the pharmacological inhibition of AR has been shown to reduce the frequency of polyneuropathy and retinopathy in DM patients (Bhatnagar & Srivastava, 1992, Biochem. Med. Metab. Biol. 48:91-121; Baynes & Thorpe, 1999, Diab. 48:1-9; Ramana et al., 2002, J. Biol. Chem. 277:32063-32070). In fact, it has been shown that human AR expression in transgenic mice accelerates the diabetic atherosclerosis (Vikramadithyan et al., 2005, J. Clin. Invest. 115:2434-2443), implying that AR may play an important role in atherothrombosis.

There is a need in the art to develop a novel method of preventing or treating abnormal thrombus formation and subsequent cardiovascular disease in diabetic patients and patients with increased cardiovascular risk, such as patients with coronary syndrome, cerebrovascular disease (such as stroke), peripheral vascular disease and coronary artery disease. The present invention fulfills this need.

BRIEF SUMMARY OF THE INVENTION

The invention includes a method of treating or ameliorating a condition comprising platelet hyperactivity or abnormal thrombus formation in a subject in need thereof. The method comprises administering to the subject a therapeutically effective amount of a pharmaceutical composition comprising at least one aldose reductase inhibitor.

In one embodiment, the subject is diabetic or has increased cardiovascular risk. In another embodiment, the subject has been diagnosed with cerebrovascular disease, peripheral vascular disease or coronary artery disease. In yet another embodiment, the at least one aldose reductase is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof. In yet another embodiment, the at least one aldose reductase is selected from the group consisting of an aldose reductase antibody, siRNA, ribozyme, an antisense, an aptamer, a peptidomimetic, and any combinations thereof. In yet another embodiment, the method further comprises administering to the subject aspirin or a salt thereof. In yet another embodiment, the method further comprises administering to the subject a selective NSAID COX-1 inhibitor or a salt thereof. In yet another embodiment, the pharmaceutical composition and the aspirin are co-administered to the subject. In yet another embodiment, the pharmaceutical composition and the aspirin are co-formulated and co-administered to the subject. In yet another embodiment, administering aspirin or a salt thereof to the subject does not treat or ameliorate the condition comprising platelet hyperactivity or abnormal thrombus formation in the subject. In yet another embodiment, the subject has an elevated level of TX-M. In yet another embodiment, the subject has a level of TX-M that is at least about 25% higher than the average level of TX-M in a normal subject. In yet another embodiment, the subject has a level of TX-M that is at least about 50% higher than the average level of TX-M in a normal subject. In yet another embodiment, the subject has a level of TX-M that is at least about 75% higher than the average level of TX-M in a normal subject. In yet another embodiment, the subject has a level of TX-M that is at least about 100% higher than the average level of TX-M in a normal subject. In yet another embodiment, administering of aspirin or a salt thereof to the subject has no or minimal effect on the elevated levels of TX-M in the subject. In yet another embodiment, the subject is a mammal. In yet another embodiment, the mammal is human. In yet another embodiment, the pharmaceutical composition is administered to the subject by an administration route selected from the group consisting of inhalational, oral, rectal, vaginal, parenteral, topical, transdermal, pulmonary, intranasal, buccal, ophthalmic, intrathecal, and any combinations thereof.

The invention further includes a pharmaceutical composition comprising at least one aldose reductase inhibitor and aspirin or a salt thereof. In one embodiment, the at least one aldose reductase inhibitor is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof.

The invention further includes a kit comprising at least one aldose reductase inhibitor, aspirin or a salt thereof, an applicator, and an instructional material for use thereof. In one embodiment, the at least one aldose reductase inhibitor is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof. In another embodiment, the instructional material comprises instructions for treating or ameliorating a condition comprising platelet hyperactivity or abnormal thrombus formation in a subject in need thereof. In yet another embodiment, the subject is diabetic or has increased cardiovascular risk. In yet another embodiment, the subject has been diagnosed with cerebrovascular disease, peripheral vascular disease or coronary artery disease. In yet another embodiment, the at least one aldose reductase inhibitor and aspirin are co-formulated. In yet another embodiment, the instructional material further recites that the kit is to be used if administering of aspirin or a salt thereof to the subject does not treat or ameliorate the condition comprising platelet hyperactivity or abnormal thrombus formation in the subject. In yet another embodiment, the instructional material further recites that the kit is to be used if the subject has an elevated level of TX-M. In yet another embodiment, the instructional material further recites that the kit is to be used if administering of aspirin or a salt thereof to the subject has no or minimal effect on the elevated level of TX-M in the subject. In yet another embodiment, the subject is a mammal. In yet another embodiment, the mammal is human. In yet another embodiment, the at least one aldose reductase inhibitor is administered to the subject by an administration route selected from the group consisting of inhalational, oral, rectal, vaginal, parenteral, topical, transdermal, pulmonary, intranasal, buccal, ophthalmic, intrathecal, and any combination thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIGS. 2A-2F, illustrates glucose-induced platelet activation and aggregation in response to 1 µg/mL collagen or 1 µM ADP. The platelet suspensions were incubated with 5.5 mmol/L, 15 mmol/L or 25 mmol/L glucose for 90 min. The percentage of light transmission, an index of platelet aggregation, was measured in platelet suspensions in response to (FIG. 2A) 1 µg/mL collagen or (FIG. 2B) 1 µM ADP for 10 min. FIG. 2C: Quantification of data was presented as the percentage of light transmission. Data are expressed as mean±SE (n=5 healthy subjects). *$P<0.001$ & $P<0.01$ compared with 5.5 mM glucose; #$P<0.05$ compared with 15 mM glucose. The P-selectin translocation to membrane was assessed by flow cytometry after stimulation with (FIG. 2D) 1 µg/mL collagen or (FIG. 2E) 1 µM ADP. The representative overlay plots were presented as the number of events over the log of associated fluorescence (Baseline refers to the group without collagen or ADP stimulation). FIG. 2F: Quantification of data was presented as mean fluorescent intensity (MFI). Data are expressed as mean±SE (n=5 healthy subjects). *$P<0.001$ & $P<0.01$ compared with 5.5 mM glucose; ##$P<0.05$ compared with 15 mM glucose. $^{\$\$\$}$represents significant difference ($P<0.001$) from baseline.

FIG. 3, comprising FIG. 3C: Quantification of data from 1 µg/mL collagen was expressed as aggregation in percentage of light transmission. Data are expressed as mean±SE (n=5 healthy subjects). *$P<0.001$ & $P<0.01$ compared with the vehicle incubated in 5.5 mM glucose; ####$P<0.001$ & ###$P<0.01$ compared with the vehicle incubated in 25 mM glucose. The P-selectin translocation to membrane was assessed by flow cytometry. The representative overlay plots in (FIG. 3D) NG and (FIG. 3E) HG groups in the presence or absence of 10 µmol/L epalrestat (ARI) were presented as the number of events over the log of associated fluorescence (Baseline refers to the group without collagen stimulation). FIG. 3F: Quantification of data was presented as mean fluorescent intensity (MFI). Data are expressed as mean±SE (n=5 healthy subjects). ***$P<0.001$ compared with the control in 5.5 mM glucose; ####$P<0.001$ compared with the control incubated in 25 mM glucose.

FIGS. 4A-4B, illustrate responses to collagen. FIG. 4A: Activity of aldose reductase in the human platelets in response to 1 µg/mL collagen under NG & HG condition. Platelet suspensions were incubated with NG or HG for 90 min in the presence or absence of 10 mmol/L epalrestat (ARI), prior to stimulation by 1 µg/mL collagen for 10 min. Data are expressed as mean±SE (n=5 healthy subjects). *$P<0.001$, $P<0.01$ & *$P<0.05$ compared with values incubated in NG alone; ####$P<0.001$ compared with values in NG & HG with the addition of 1 µg/mL collagen respectively. FIG. 4B: Expression of AR in the human platelets in response to 1 µg/mL collagen. Platelet suspensions were incubated with NG or HG for 90 min, prior to stimulation by 1 µg/mL collagen for 10 min, and the total cellular extract was collected for experiments. Data are expressed as mean±SE (n=5 healthy subjects). *$P<0.001$ & $P<0.01$ compared with values incubated in NG.

FIG. 5, comprising FIG. 5A: The phosphorylation of different kinases in collagen-stimulated platelets under NG condition was assayed by human phosphokinase array kits. Representative results are shown. FIG. 5B: The phosphorylation of p38α MAPK was further measured by Western blot using specific antibody for its phosphorylated form. Data are expressed as mean±SE (n=5 healthy subjects). *$P<0.001$ compared with values incubated in NG alone; ####$P<0.001$ compared with values in NG with the addition of 1 μg/mL collagen; $^{\$\$\$}$P<0.001 compared with values in HG with the addition of 1 μg/mL collagen. FIG. 5C: Platelet suspensions were incubated with NG or HG for 90 min in the presence or absence of 50 μmol/L SB239063 (trans-4-[4-(4-fluorophenyl)-5-(2-methoxy-4-pyrimidinyl)-1H-imidazol-1-yl]cyclohexanol), prior to stimulation by 1 μg/mL collagen. The platelet aggregation was presented as the percentage of light transmission, and measured in platelet suspensions under NG or HG condition in response to 1 μg/mL collagen for 5 min. Data are expressed as mean±SE (n=5 healthy subjects). *P<0.001 compared with vehicle incubated in NG; $^{\#\#\#}$P<0.001 compared with vehicle incubated in HG.

FIG. 6, comprising FIGS. 6A-6C, illustrates the finding that AR contributes to the oxidative stress in collagen-stimulated platelets. Platelet suspensions were incubated with NG or HG for 90 min in the presence and absence of 10 μmol/L epalrestat (ARI), 1 mmol/L N-acetyl-cysteine (NAC) & 100 μmol/L apocynin (Apo). (FIG. 6A) The washed platelets were incubated with 1 μmol/L ROS/Superoxide detection mix for 60 min at 37° C. in the presence or absence of 1 μg/mL collagen for 10 min. The quantification of data for ROS was shown in left panel, and that for superoxide was shown in right panel. Data are expressed as mean±SE (n=5 healthy subjects). *P<0.001, P<0.01 & *P<0.05 compared with values incubated in NG alone; $^{\#\#\#}$P<0.001 & $^{\#}$P<0.05 compared with values in NG with the addition of 1 μg/mL collagen; $^{\$\$\$}$P<0.01 compared with values in HG with the addition of 1 μg/mL collagen. FIG. 6B: The aggregation was expressed as the percentage of light transmission, and measured in platelet suspensions under NG or HG condition. FIG. 6C: the level of thromboxane was assayed in the supernatant. ***P<0.001 compared with values incubated in NG with the addition of 1 μg/mL collagen; $^{\#\#\#}$P<0.001 compared with values in HG with the addition of 1 μg/mL collagen.

FIG. 7, comprising, FIG. 7A: Platelet suspensions were incubated with NG or HG for 90 min in the presence and absence of 10 μmol/L epalrestat (ARI), prior to stimulation by 1 μg/mL collagen for 10 min, and the total extract was harvested for experiments. Data are expressed as mean±SE (n=5 healthy subjects). *P<0.001 & P<0.01 compared with values incubated in NG alone; $^{\#\#\#}$P<0.001 compared with values in NG with the addition of 1 μg/mL collagen; $^{\$\$}$P<0.01 compared with values in HG with the addition of 1 μg/mL collagen. FIG. 7B: inhibition of the upstream pathway of p38α MAPK attenuated its phosphorylation in collagen-stimulated platelets. Platelet suspensions were incubated with NG or HG for 90 min in the presence of 5 mol/L U73122, 1 mmol/L N-acetyl-cysteine (NAC) and 10 μmol/L quercetin, prior to stimulation by 1 μg/mL collagen for 10 min, and the total extract was harvested for experiments. Data are expressed as mean±SE (n=5 healthy subjects). ***P<0.001 & *P<0.05 compared with values incubated in NG or HG alone respectively; $^{\#\#\#}$P<0.001 compared with values in NG or HG with the addition of 1 μg/mL collagen respectively.

FIG. 8, comprising FIGS. 8A-8D, illustrates the finding that AR is required for the intracellular translocation of PKC isoforms (α, βII & δ) in collagen-stimulated platelets. Platelet suspensions were incubated with NG or HG for 90 min in the presence and absence of 10 μmol/L epalrestat (ARI), prior to stimulation by 1 μg/mL collagen for 10 min, and the membrane and cytosolic fractions were harvested for experiments. Data are expressed as mean±SE (n=5 healthy subjects). ***P<0.001 compared with values incubated in NG alone; $^{\#\#\#}$P<0.001 & $^{\#\#}$P<0.01 compared with values in NG with the addition of 1 μg/mL collagen; $^{\$\$\$}$P<0.01 & $^{\$\$}$P<0.01 compared with values in HG with the addition of 1 μg/mL collagen.

FIG. 9, comprising FIG. 9C: the expression of TX receptor was assessed in the membrane and cytosolic fractions. Data are expressed as mean±SE (n=5 healthy subjects). *P<0.001 compared with values incubated in HG alone; $^{\#\#\#}$P<0.001 compared with values in HG with the addition of 1 μg/mL collagen.

FIG. 10, comprising FIG. 10A: the platelet aggregation was presented as the percentage of light transmission, and measured in platelet suspensions under NG or HG condition in response to 1 μg/mL collagen for 5 min FIG. 10B: after stimulation, the supernatant was harvested for the measurement of TX generation. Data are expressed as mean±SE (n=6). *P<0.001 compared with vehicle incubated in NG; $^{\#\#\#}$P<0.001 compared with vehicle incubated in HG. FIG. 10C**: correlation of thromboxane release with increased platelet aggregation in collagen-stimulated human platelets. Platelet suspensions were incubated with NG or HG for 90 min, prior to stimulation by 1 μg/mL collagen for 10 min, and the percentage of light transmission was also measured in platelet suspensions, and the thromboxane release was assayed in the supernatant.

FIGS. 11A-11B, illustrates the finding that increased urinary thromboxane metabolite in patient with (FIG. 11A) deep venous (DV) thrombosis or (FIG. 11B) coronary artery bypass graft (CABG) thrombosis. For patients with DV thrombosis, the level of urinary thromboxane metabolite was measured as an index of thromboxane release in diabetic (DM) patient with or without DV thrombosis (n=2 & n=3 respectively) compared to non-DM patients with or without DV thrombosis (n=32 & n=20 respectively). For patients with CABG thrombosis, the level of urinary thromboxane metabolite was measured in diabetic (DM) patient with or without CABG thrombosis (n=28 & n=75 respectively) compared to non-DM patients with or without CABG thrombosis (n=68 & n=120 respectively). Data are expressed as median with interquartile range. A difference of P<0.05 was considered as significant.

FIG. 15, comprising FIG. 15A: the level of AR knockdown by siRNA was determined by Western blot analysis. FIG. 15B: the representative overlay plots were presented as the number of events over the log of associated fluorescence (Baseline refers to the untransfected MEG-1 cells without collagen stimulation). FIG. 15C: quantification of data was presented as mean fluorescent intensity (MFI). Data are expressed as mean±SE (n=3). ***P<0.001 compared with the baseline; ##P<0.01 compared with the control siRNA group.

FIG. 16, comprising FIGS. 16A-16D, illustrates the finding that AR is required for the phosphorylation of PKC isoforms (α, βII & δ) in collagen-stimulated platelets. Platelet suspensions were incubated with NG or HG for 90 min in the presence and absence of 10 µmol/L epalrestat (ARI), prior to stimulation by 1 µg/mL collagen for 10 min, and the total cellular extract was harvested for experiments. Data are expressed as mean±SE (n=5 healthy subjects). *P<0.001, P<0.01 & *P<0.05 compared with values incubated in NG alone; ###P<0.001 & #P<0.05 compared with values in NG with the addition of 1 µg/mL collagen; $$$P<0.01 compared with values in HG with the addition of 1 µg/mL collagen.

DETAILED DESCRIPTION OF THE INVENTION

The present invention relates to the unexpected discovery that, in human platelets, aldose reductase (AR) modulates platelet response synergistically to both hyperglycemia and collagen exposure, through a pathway involving ROS/ PLCγ2/PKC/p38 MAPK. As demonstrated herein, clinical studies in patients with platelet activation (deep vein thrombosis, and patients with saphenous vein graft occlusion after coronary bypass surgery) indicated that significant increases in urinary levels of a major enzymatic metabolite of TX (i.e., 11-dehydro-$TXB_2$, TX-M), particularly in diabetic patients (even in the presence of low dose aspirin). This suggests that many subjects with persistently raised TX-M despite the use of low dose aspirin may have underlying collagen exposure with thrombovascular disease (reflecting endothelial damage). In one embodiment, a subject with persistently raised TX-M has a TX-M level at least about 50% higher than the average TX-M level in a normal subject. In another embodiment, a subject with persistently raised TX-M has a TX-M level at least about 25% higher than the average TX-M level in a normal subject. In yet another embodiment, a subject with persistently raised TX-M has a TX-M level at least about 75% higher than the average TX-M level in a normal subject. In yet another embodiment, a subject with persistently raised TX-M has a TX-M level at least about 100% higher than the average TX-M level in a normal subject. The results described herein provide multiple signaling targets for combination chemotherapy to inhibit the synergistic platelet activation observed with hyperglycemia and collagen exposure.

Figure 19:
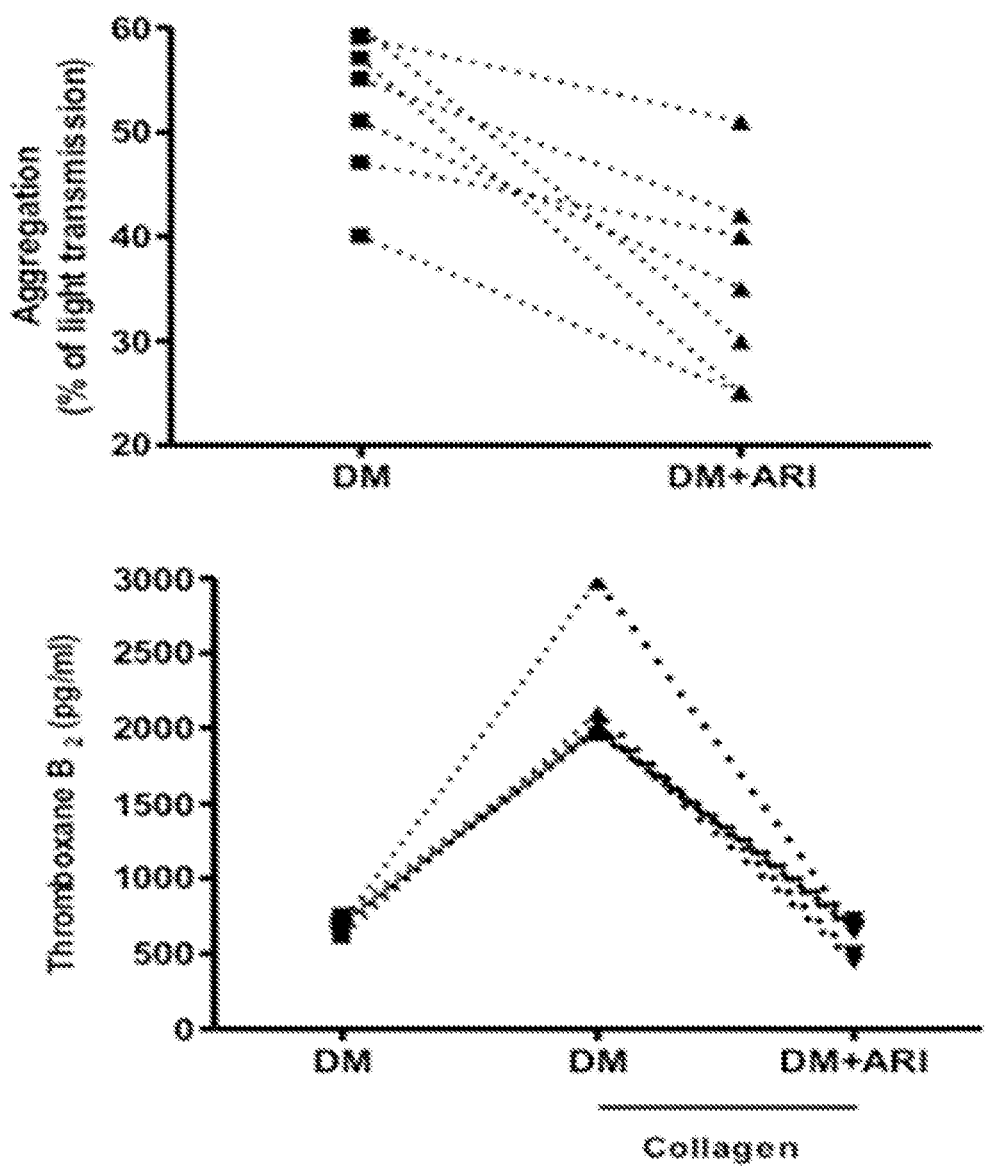
FIG. 19 is a graph illustrating experiments performed with platelets from a diabetic patient. The top graph illustrates the finding that addition of an aldose reductase inhibitor (epalrestat at 10 µmol/L) prior to collagen stimulation (1 µg/mL). reduced in vitro aggregation of these platelets. The bottom graph illustrates the finding that addition of an aldose reductase inhibitor reduced in vitro release of thromboxane $B_2$ induced by exposure of these platelets to collagen.

In one aspect, the present invention provides a method of treating or preventing abnormal thrombus formation and subsequent cardiovascular disease in diabetic patients and patients with increased cardiovascular risk such as patients with cerebrovascular, peripheral vascular, and coronary artery disease. The method comprises administering to the patient an aldose reductase inhibitor (ARI), including but not limited to epalrestat, alone or in conjunction with other anti-platelet agents. The present invention also provides new therapeutic intervention targets by demonstrating the mechanism by which ARIs prevent the signal transduction of an acute hyperglycemic pathway that leads to prevention of thromboxane (TX) release, thromboxane receptor (TP) increase, and thus prevention of platelet aggregation increase (FIG. 19).

Diabetes mellitus leads to increased morbidity from cardiovascular disease. The studies described herein elucidated the mechanism by which hyperglycemia increases platelet hyperactivity, identifying aldose reductase as the master switch that transduces the high glucose signal to increase thromboxane production and ultimately platelet activity. Since aspirin alone is not effective as an antiplatelet agent in many diabetic patients, particularly those with increased collagen exposure, aldose reductase antagonists alone or in combination with other anti-platelet agents, such as aspirin or primary and secondary prevention of cardiovascular disease, may be used to treat or prevent abnormal thrombus formation and subsequent cardiovascular disease, particularly in diabetic patients with evidence of endothelial damage.

While epalrestat, and other aldose reductase inhibitors are currently in use for the treatment of diabetic neuropathy, they have not been shown to be effective in cardiovascular disease. Aspirin and other anti-platelet agents are prescribed prophylactically in patients with the high cardiovascular risk for both primary and secondary prevention of cardiovascular events. This invention demonstrates that Epalrestat is more effective than aspirin alone in decreasing platelet aggregation under hyperglycemic conditions. In one embodiment, aldose reductase inhibitors are effective in treating patients with high cardiovascular risk for both primary and secondary prevention of cardiovascular events, Definitions As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element.

A "subject" or "individual" or "patient," as used therein, can be a human or non-human mammal. Non-human mammals include, for example, livestock and pets, such as ovine, bovine, porcine, canine, feline and murine mammals. Preferably, the subject is human.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "DM" refers to diabetes mellitus.

As used herein, the term "AR" refers to aldose reductase.

As used herein, the term "ARI" refers to aldose reductase inhibitor.

As used herein, the term "TM-X" refers to 11-dehydrothromboxane $B_2$ or a salt thereof.

As used herein, the term "IDD 676" refers to lidorestat or a salt thereof.

As used herein, the term "IDD 63" refers to tolrestat or a salt thereof.

As used herein, the term "IDD 65" refers to zopolrestat or a salt thereof.

As used herein, the term "IDD 60" refers to sorbinil or a salt thereof.

As used herein, the term "IDD 62" refers to minalrestat or a salt thereof.

As used herein, the term "IDD 73" refers to risarestat or CT-112, or a salt thereof.

As used herein, the term "IDD 148" refers to zenarestat, or a salt thereof.

As used herein, the term "IDD 314" or "IDD 149" refers to NZ 314, or a salt thereof.

As used herein, the term "SB239063" refers to (trans-4-[4-(4-fluorophenyl)-5-(2-methoxy-4-pyrimidinyl)-1H-imidazol-1-yl]cyclohexanol) or a salt thereof.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a "normal" subject with respect to the disease or disorder does not present the characteristic symptoms, effects or markers of the disease or disorder.

As used herein, the term "treatment" or "treating" is defined as the application or administration of a therapeutic agent, i.e., a compound useful within the invention (alone or in combination with another pharmaceutical agent), to a subject, or application or administration of a therapeutic agent to an isolated tissue or cell line from a subject (for example, for diagnosis or ex vivo applications), who has diabetes, a symptom of diabetes or the potential to develop diabetes, with the purpose to prevent, cure, heal, alleviate, relieve, alter, remedy, ameliorate, improve or affect abnormal thrombus formation and/or cardiovascular disease, the symptoms of abnormal thrombus formation and/or cardiovascular disease or the potential to develop abnormal thrombus formation and/or cardiovascular disease. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

As used herein, the terms "effective amount" or "therapeutically effective amount" or "pharmaceutically effective amount" of a compound are used interchangeably to refer to the amount of the compound that is sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation. By the term "specifically bind" or "specifically binds," as used herein, is meant that a first molecule (for example, an antibody) preferentially binds to a second molecule (for example, a particular antigenic epitope), but does not necessarily bind only to that second molecule.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "antibody," as used herein, refers to an immunoglobulin molecule able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "applicator," as the term is used herein, is meant any device including, but not limited to, a hypodermic syringe, a pipette, and the like, for administering the compounds and compositions of the invention.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example, by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In one embodiment, a composition useful within the methods of the invention comprises at least one aldose reductase inhibitor or a salt thereof. In another embodiment, an aldose reductase inhibitor is an antibody that binds to and neutralizes aldose reductase. In another embodiment, the agent is a chemical compound that inhibits aldose reductase. In yet another embodiment, the agent reduces the expression or production of aldose reductase in the subject. Agents that reduce the expression, production and/or circulating concentration of aldose reductase by any physiological mechanism are considered useful within the methods of the invention.

Non-limiting examples of aldose reductase inhibitors contemplated within the methods of the invention are:

Tolrestat (also known as AY-2773): N-{[6-methoxy-5-(trifluoromethyl)-1-naphthyl]carbothioyl}-N-methylglycine, or a salt thereof;

Epalrestat: 2-[(5Z)-5-[(E)-3-phenil-2-methylprop-2-enylidene]-4-oxo-2-thioxo-3-thiazolidinyl]acetic acid, or a salt thereof;

Ranirestat (also known as AS-3201): (3R)-2'-(4-bromo-2-fluorobenzyl)-1'H,2H,5H-spiro[pyrrolidine-3,4'-pyrrolo[1,2-a]pyrazine]-1',2,3',5(2'H)-tetrone, or a salt thereof;

Fidarestat (also known as SNK-860): (2S,4S)-6-fluoro-2',5'-dioxospiro[2,3-dihydrochromene-4,4'-imidazolidine]-2-carboxamide, or a salt thereof;

Lidorestat: [3-(4,5,7-Trifluorobenzothiazol-2-ylmethyl)indol-1-yl]acetic acid, or 3-[(4,5,7-Trifluorobenzothiazol-2-yl)methyl]indole-N-acetic acid, or a salt thereof;

Zopolrestat: 3,4-Dihydro-4-oxo-3-[[5-(trifluoromethyl)-2-benzothiazolyl]methyl]-1-phthalazineacetic acid, or a salt thereof;

Sorbinil: (4S)-6-Fluoro-2,3-dihydro-2'H,5'H-spiro[chromene-4,4'-imidazolidine]-2',5'-dione, or a salt thereof;

Minalrestat: (±)-2-(4-Bromo-2-fluorobenzyl)-6-fluorospiro[1,2,3,4-tetrahydroisoquinoline-4,3'-pyrrolidine]-1,2',3,5'-tetraone or (±)-2-[(4-Bromo-2-fluorophenyl)methyl]-6-fluorospiro[isoquinoline-4(1H), 3'-pyrrolidine]-1,2',3,5' (2H)-tetraone, or a salt thereof;

Risarestat: 5-[3-Ethoxy-4-(pentyloxy)phenyl]-2,4-thiazolidinedione, or a salt thereof;

Zenarestat: 3-(2-Fluoro-4-bromobenzyl)-7-chloro-2,4(1H,3H)-dioxoquinazoline-1-acetic acid; or 3-[(4-Bromo-2-fluorophenyl)methyl]-7-chloro-3,4-dihydro-2,4-dioxo-1 (2H)-quinazolineacetic acid, or a salt thereof;

NZ-314: 3-(3-nitrobenzyl)-2,4,5-trioxoimidazolidine-1-acetic acid, or a salt thereof.

Structural analogs, derivatives, prodrugs, salts and solvates of these compounds are also contemplated within the invention. Foe r examples, esters of these compounds (such as methyl, ethyl, isopropyl, n-butyl and n-pentyl esters) are contemplated within the invention.

The compositions useful within the invention optionally further comprise aspirin (also known as acetylsalicylic acid)

or a salt thereof. Other selective NSAID COX-1 are also useful within the methods of the invention. In one embodiment, the invention includes a pharmaceutical composition comprising at least one aldose reductase inhibitor and aspirin or a salt thereof. In another embodiment, the at least one aldose reductase inhibitor is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof.

Description

Diabetes mellitus is associated with platelet hyperactivity, leading to increased morbidity and mortality from cardiovascular disease. Although intensely studied, the mechanism for the relationship between hyperglycemia, thromboxane (TX) generation, and platelet hyperactivity remains unclear. The studies reported herein identified key signaling components that transduce high glucose signal into thromboxane (TX) generation and determine the clinical implications. As shown herein, in human platelets aldose reductase (AR) modulates platelet response synergistically, to both hyperglycemia and collagen exposure, through a pathway involving ROS/PLCγ2/PKC/p38 MAPK. These results were supported with clinical studies in patients with platelet activation (deep vein thrombosis, and patients with saphenous vein graft occlusion after coronary bypass surgery) where significant increases in urinary levels of a major enzymatic metabolite of TX (i.e., 11-dehydro-$TXB_2$, TX-M) were observed, particularly in diabetic patients (even in the presence of low dose aspirin). Many patients with persistently raised TX-M, despite the use of low dose aspirin, may have underlying collagen exposure with thrombovascular disease (reflecting endothelial damage). The studies described herein provide multiple signaling targets for combination chemotherapy to inhibit the synergistic platelet activation observed with hyperglycemia and collagen exposure.

Methods of the Invention

The invention includes a method of treating or ameliorating a condition comprising platelet hyperactivity or abnormal thrombus formation in a subject in need thereof. The method comprises administering to the subject a therapeutically effective amount of a pharmaceutical composition comprising at least one aldose reductase inhibitor.

In one embodiment, the subject is diabetic or has increased cardiovascular risk. In another embodiment, the subject has been diagnosed with cerebrovascular disease, peripheral vascular disease or coronary artery disease. In yet another embodiment, the at least one aldose reductase is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof. In yet another embodiment, the at least one aldose reductase is selected from the group consisting of an aldose reductase antibody, siRNA, ribozyme, an antisense, an aptamer, a peptidomimetic, and any combinations thereof. In yet another embodiment, the method further comprises administering to the subject aspirin or a salt thereof. In yet another embodiment, the pharmaceutical composition and the aspirin are co-administered to the subject. In yet another embodiment, the pharmaceutical composition and the aspirin are co-formulated and co-administered to the subject. In yet another embodiment, administering aspirin or a salt thereof to the subject does not treat or ameliorate the condition comprising platelet hyperactivity or abnormal thrombus formation in the subject. In yet another embodiment, the subject has an elevated level of TX-M. In yet another embodiment, administering of aspirin or a salt thereof to the subject has no or minimal effect on the elevated level of TX-M in the subject.

In yet another embodiment, the subject is a mammal. In yet another embodiment, the mammal is human. In yet another embodiment, the pharmaceutical composition is administered to the subject by an administration route selected from the group consisting of inhalational, oral, rectal, vaginal, parenteral, topical, transdermal, pulmonary, intranasal, buccal, ophthalmic, intrathecal, and any combinations thereof.

Kits of the Invention

The invention includes a kit comprising at least one aldose reductase inhibitor, aspirin or a salt thereof, an applicator, and an instructional material for use thereof.

In one embodiment, the at least one aldose reductase inhibitor is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof. In yet another embodiment, the at least one aldose reductase inhibitor is selected from the group consisting of an aldose reductase antibody, siRNA, ribozyme, an antisense, an aptamer, a peptidomimetic, a small molecule, and any combination thereof. In yet another embodiment, the at least one COX-1 inhibitor is selected from the group consisting of a COX-1 antibody, siRNA, ribozyme, an antisense, an aptamer, a peptidomimetic, a small molecule, and any combination thereof. In yet another embodiment, the antibody is selected from the group consisting of a polyclonal antibody, monoclonal antibody, humanized antibody, synthetic antibody, heavy chain antibody, human antibody, biologically active fragment of an antibody, and any combination thereof. In yet another embodiment, the instructional material comprises instructions for treating or ameliorating a condition comprising platelet hyperactivity or abnormal thrombus formation in a subject in need thereof. In yet another embodiment, the instructional material recites that the compositions of the invention are useful to treat or prevent abnormal thrombus formation and subsequent cardiovascular disease in diabetic patients and patients with increased cardiovascular risk, such as patients with coronary syndrome, cerebrovascular disease (such as stroke), peripheral vascular disease and coronary artery disease.

In yet another embodiment, the subject is diabetic or has increased cardiovascular risk. In yet another embodiment, the subject has been diagnosed with cerebrovascular disease, peripheral vascular disease or coronary artery disease. In yet another embodiment, the at least one aldose reductase inhibitor and aspirin are co-formulated. In yet another embodiment, the instructional material further recites that the kit is to be used if administering of aspirin or a salt thereof to the subject does not treat or ameliorate the condition comprising platelet hyperactivity or abnormal thrombus formation in the subject. In yet another embodiment, the instructional material further recites that the kit is to be used if the subject has an elevated level of TX-M. In yet another embodiment, the instructional material further recites that the kit is to be used if administering of aspirin or a salt thereof to the subject has no or minimal effect on the elevated level of TX-M in the subject. In yet another embodiment, the subject is a mammal. In yet another embodiment, the mammal is human. In yet another embodiment, the at least one aldose reductase inhibitor is administered to the subject by an administration route selected from the group consisting of inhalational, oral, rectal, vaginal, parenteral, topical, transdermal, pulmonary, intranasal, buccal, ophthalmic, intrathecal, and any combination thereof.

Combination Therapies

The compounds identified using the methods described here are useful in the methods of the invention in combination with at least one additional compound useful for treating platelet hyperactivity. This additional compound may comprise compounds identified herein or compounds, for example, commercially available compounds, known to treat, prevent, or reduce the symptoms of platelet hyperactivity.

In one aspect, the present invention contemplates that the aldose reductase inhibitors useful within the invention may be used in combination with a therapeutic agent that is known to reduce platelet hyperactivity, including but not limited to aspirin or a salt thereof or a selective NSAID COX-1 inhibitor or a salt thereof.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Formulations

The invention envisions the use of a pharmaceutical composition comprising at least one aldose reductase inhibitor or a salt thereof within the methods of the invention. Optionally, the pharmaceutical composition further comprises at least one COX-1 inhibitor or a salt thereof.

Such a pharmaceutical composition comprises at least one aldose reductase inhibitor or a salt thereof, in a form suitable for administration to a subject, or the pharmaceutical composition may comprise at least one aldose reductase inhibitor or a salt thereof, and one or more pharmaceutically acceptable carriers, one or more additional ingredients, or some combination of these. The at least one aldose reductase inhibitor may be present in the pharmaceutical composition in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, parenteral, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (for example, about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions are formulated using one or more pharmaceutically acceptable excipients or carriers. In one embodiment, the pharmaceutical compositions comprise a therapeutically effective amount of at least one aldose reductase inhibitor and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it ispreferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, for example, lubricants, preservatives, stabilizers, wetting agents, emulsifiers, salts for influencing osmotic pressure buffers, coloring, flavoring and/or aromatic substances and the like. They may also be combined where desired with other active agents, for example, other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example, in Genaro, ed., 1985, Remington's Pharmaceutical Sciences, Mack Publishing Co., Easton, Pa., which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent that inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (for example, disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (for example, polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one that comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. For example, the therapeutic formulations may be administered to the patient either prior to or after a surgical intervention related to platelet hyperactivity, or shortly after the patient was diagnosed with platelet hyperactivity. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, for example, physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of platelet hyperactivity in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of platelet hyperactivity in a patient.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, for example, treating, preventing, or reducing cancer in a patient.

Routes of Administration

Routes of administration of any of the compositions of the invention include inhalational, oral, nasal, rectal, parenteral, sublingual, transdermal, transmucosal (for example, sublingual, lingual, (trans)buccal, (trans)urethral, vaginal (for example, trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients suitable for the manufacture of tablets. Such excipients include, for example, an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (for example, OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (for example, sorbitol syrup, methyl cellulose or hydrogenated edible fats); emulsifying agent (for example, lecithin or acacia); non-aqueous vehicles (for example, almond oil, oily esters or ethyl alcohol); and preservatives (for example, methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid.

Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (for example, sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin.

Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example, pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form. For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation. In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, for example, nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods:

Drugs & Inhibitors

The AR inhibitor Epalrestat and the NAD(P)H oxidase inhibitor Apocynin were purchased from Santa Cruz Biotechnology. The antioxidant N-acetyl-cysteine (NAC) was from Fisher Scientific. The p38 MAPK inhibitor SB239063 and the phospholipase C inhibitor U73122 were from Calbiochem (San Diego, Calif.). The thromboxane receptor antagonist SQ29548 was from Cayman Chemical (Ann Arbor, Mich.). Aspirin (Acetylsalicylic Acid; ASA) and the AR inhibitor Quercetin were from MP Biomedicals (Solon, Ohio).

Preparation of Human Platelets

Venous blood was drawn from volunteers at Yale University Medical School, free from medication known to interfere with platelet function. Platelet-rich plasma (PRP) was prepared from blood (27 mL) that was drawn by venipuncture into 3 ml of 3.8% trisodium citrate (w/v). PRP was obtained by centrifugation of blood at 250 g at 37° C. for 15 min and the platelet count in the PRP was estimated by an automated cell counter.

Platelet-poor plasma (PPP) was obtained by centrifugation of the rest of the blood at 1400 g at 25° C. for 10 min. The PRP was adjusted with PPP to $2-3\times10^8$ platelets/mL suspensions. For the washed platelets, PRP was obtained by centrifugation at 250 g for 15 min, and platelets were sedimented at 1,000 g for 15 min, and then resuspended in washing buffer (103 mmol/L NaCl, 5 mmol/L KCl, 1 mmol/L $MgCl_2$, 5 mmol/L glucose, 36 mmol/L citric acid) at pH 6.5 containing 3.5 mg/mL bovine serum albumin (Sigma). After sedimentation, the platelets were washed twice in this buffer and resuspended at $2-3\times10^8$ platelets/mL in the buffer composed of 5 mmol/L HEPES, 137 mmol/L NaCl, 2 mmol/L KCl, 1 mmol/L $MgCl_2$, 12 mmol/L $NaHCO_3$, 0.3 mmol/L $NaH_2PO_4$, 5.5 mmol/L glucose, pH 7.4, containing 3.5 mg/mL BSA (Saxena et al., 1989, Science 243:1596-1599).

Measurement of Platelet Aggregation

Platelet suspensions were incubated with 5 or 25 mmol/L glucose in the presence or absence of 1 μmol/L or 10 μmol/L epalrestat for 90 min. Platelet aggregation was monitored at 37° C. with constant stirring (1,200 rpm) in a dual-channel Lumi-aggregometer (Chrono-Log model 700). Platelet aggregation was measured as the increase in light transmission for 10 min, starting with the addition of 0.5 μL of 1 mg/mL collagen (Chrono-Log) as a proaggregatory stimulus. For measuring ADP-stimulated platelet aggregation, 1 μM ADP (Chrono-Log) was used. The maximum aggregation was expressed as percentage of maximum light transmission, with non-stimulated platelet-rich plasma being 0% and platelet-poor plasma 100%.

Determination of Platelet Activation

P-selectin translocation was assessed by flow cytometry using monoclonal antibody against P-selectin (fluorescein isothiocyanate-conjugated, Biolegend) as described previously (Caron et al., 2002, J. Cardiovasc. Pharmacol. 40:296-306; Theoret et al., 2001, J. Pharmacol. Exp. Ther. 298:658-664) with minor modifications. Briefly, platelet suspensions were pre-incubated with 5 or 25 mmol/L glucose in the presence or absence of 1 or 10 μmol/L epalrestat for 90 min, prior to stimulation by 1 μg/mL collagen for 10 min. The samples were then washed and fixed in 1% paraformaldehyde for 1 hr at 4° C. The fixed platelets were then washed and labeled with saturating concentrations of monoclonal antibody for 1 hr. All the samples were analyzed on a flow cytometer (FACS Calibur). Platelets were identified and gated by their characteristic forward and side scatter properties and 20,000 platelets were analyzed from each sample.

Western Blotting

Platelets were homogenized in the lysis buffer (25 mmol/L Tris HCl, pH 7.6, 150 mmol/L NaCl, 1% NP-40, 1% sodium deoxycholate, 0.1% SDS) with the addition of 0.1% protease inhibitor and 0.1% phosphatase inhibitor (Thermo Scientific). The supernatant was collected after centrifugation at 13,000 rpm for 15 min at 4° C. The samples are loaded in 4×SDS-Laemmli sample buffers and boiled for 10 min. Equal amounts of total extracts were subjected to SDS-PAGE. The proteins were transferred to nitrocellulose membrane and probed with the indicated antibodies, and the antigen-antibody complex was detected by enhanced chemiluminescence reagents (Thermo Scientific).

Primary antibodies against the following proteins were diluted and used according to the manufacturer's instructions: AR (sc-17732, Santa Cruz Biotechnology), PKC α (sc-208, Santa Cruz Biotechnology) and its phosphorylated form (sc-136018, Thr638, Santa Cruz Biotechnology), PKC βII (NB110-57358, Novus Biologicals) and its phosphorylated form (NSB964, Thr641, Novus Biologicals), PKC δ (2058, Cell Signaling) and its phosphorylated form (9376, Ser643, Cell Signaling), PLC-γ1 (H00005335-A01, Novus Biologicals) and its phosphorylated form (07866, Tyr783, Millipore), PLC-γ2 (NB110-66669, Novus Biologicals) and its phosphorylated form (NB110-57424, Tyr1217, Novus Biologicals), p38α MAPK (9212, Cell Signaling) and its phosphorylated form (AF869, T180/Y182, R&D Systems), and TX receptor (NBP1-40198, Novus Biologicals). Secondary antibodies against rabbit and mouse IgG (Thermo Scientific) were diluted 1:5000 before use. The membrane was re-probed with antibodies against $Na^+/K^+$-ATPase (NB300-147, Novus Biologicals), a plasma membrane marker, and GAPDH (sc-20357, Santa Cruz Biotechnology), a cytoplasmic marker, for normalization.

Measurement of Aldose Reductase Activity

The platelets were homogenized and centrifuged as for Western blot analysis. To determine the AR activity, a spectrophotometry measurement was used as described previously (Shinmura et al., 2002, Circ. Res. 91:240-246).

Human Phospho-Kinase Array

The human phospho-kinase array was performed according to the manufacturer's instruction (R&D Systems). Briefly, the lysates were diluted to 200 μg/mL using the specific array buffer, and mixed with a cocktail of biotinylated detection antibodies, and incubated overnight with nitrocellulose membranes spotted with capture and control antibodies. The signals for the amount of phosphorylated proteins bound were measured by the chemiluminescent detection method.

Subcellular Fractionation

Platelets were sedimented by centrifugation at 2,500 g for 5 min. The membrane and cytosolic fractions of total extracts were separated using the subcellular protein fractionation kit (Thermo Scientific). Briefly, the platelets were incubated with cytoplasmic extraction buffer for 10 min at 4° C., and then centrifuged at 500 g for 5 min. The supernatant was harvested as the cytoplasmic extract. The pellet was reconstituted with the ice-cold membrane extraction buffer, and incubated for 10 min at 4° C. After incubation, it was then centrifuged at 3000 g for 5 min, and the supernatant was harvested as the membrane extract. Aliquots (60-100 μg protein) of the soluble and the membrane fractions were separated by SDS-PAGE and subjected to Western analysis.

Measurement of Thromboxane Biosynthesis

Platelets were sedimented by centrifugation at 2,500 g for 5 min, and the supernatant was harvested for the measurement of TX levels. Since $TXA_2$ is rapidly hydrolyzed into $TXB_2$, the level of $TXB_2$ was measured using $TXB_2$ EIA kit according to the manufacturer's ELISA instructions (Cayman Chemical).

Measurement of Oxidative Stress and Superoxide Level

The oxidative stress and superoxide level was measured by a commercial kit according to the manufacturer's instruction (Total ROS/Superoxide Detection Kit, Enzo Life Sciences). Platelets were sedimented by centrifugation at 400 g for 5 min, and then washed. The washed platelets were incubated with 1 μmol/L ROS/Superoxide detection mix for 60 min at 37° C. in the presence or absence of 1 μg/mL collagen. Changes in the fluorescence intensity were measured using a microplate fluorescence reader (BioTek) at excitation/emission wavelengths of 488/520 nm (oxidative stress) and 550/610 nm (superoxide).

Genetic Knockdown of Aldose Reductase in Human Megakaryocytes (MEG-01) Culture

The MEG-01 cells (CRL-2021, ATCC) were cultured in RPMI medium. The cells were transfected with 0.1 or 0.3 mM AR siRNA (sc-37119; Santa Cruz Biotechnology) using electroporation kits (Lonza). After 48 hour incubation with RPMI medium containing 5.5 mM glucose, the P-selectin translocation to membrane was assessed by flow cytometry in response to 1 μg/mL collagen.

Patients and Study Design

Protocol for Initial Patient Study

All protocols were approved by their respective Institutional Review Boards. Patients with the presence of type 2 diabetes (n=102) were recruited from the Hospital Policlinico G.B. Rossi (Verona, Italy) and San Pio da Pietrelcina Hospital (Vasto, Italy). Exclusion criteria included concurrent cancer, inflammatory disorder, immunological disorder, surgery or major trauma in the previous month or use of nonsteroidal anti-inflammatory drugs (NSAIDs) or corticosteroids in the previous month. Both the diabetic population and the severe cardiovascular disease population were chronically treated with low dose aspirin for at least one month (enteric coated aspirin 100 mg for at least 7 consecutive days). After recruitment the patients received a standard oral dose of 100 mg for seven days at 8.00 pm. Timed urine collection (12 hours from 8.00 pm to 8.00 am) was performed on the seventh day of treatment. The 10 healthy subjects recruited were from the staff of Hospital Policlinico G.B. Rossi (Verona Italy) with normal ECG and echocardiograms and no evidence of atherosclerosis by carotid artery sonography. The healthy subjects were all treated with aspirin 100 mg daily for 1 week. Urine collection (12 hours from 8 pm to 8 am) was performed on the $7^{th}$ day of treatment.

Protocol for Studies on Deep Vein Thrombosis and Saphenous Vein Graft Occlusion

For the deep vein thrombosis clinical study, all patients with deep vein thrombosis (DVT) of the lower extremities were diagnosed with duplex ultrasound scanning or peripheral venous angiography. Exclusion criteria were concurrent infection, inflammatory condition or cancer, prolonged immobilization (i.e., lasting more than seven days) from any cause, recent trauma or surgery (i.e., within the previous three months), pregnancy, recent childbirth, or the use of oral contraceptives, at the time of the assessment. All patients abstained from the use of aspirin and other NSAIDs for at least two weeks prior to enrolment. Baseline cardiovascular characteristics were comparable for case and controls in the DVT subjects including age, cardiovascular risk factors (cigarette smoking, diabetes, hypertensive status, and lipid levels), body mass index (BMI) and systemic inflammatory status index (i.e. CRP and fibrinogen). Urinary thromboxane metabolite 11-dehydro-thromboxane B2 (TX-M) was measured by a previously validated radioimmunoassay technique (Ciabattoni et al., 1989, Biochim. Biophys. Acta 992:66-70) and expressed as a ratio of urinary creatinine.

The Reduction in Graft Occlusion Rates (RIGOR) study is a multicenter study which investigated the effects of platelet factor 4 and heparin induced antibody during saphenous vein graft (SVG) occlusion. Patients 18 years or older undergoing their first CABG surgery with saphenous vein grafts were eligible for enrolment. All patients were administered aspirin 24 hours prior to surgery and at discharge. SVG patency was assessed by multidetector computed tomography coronary angiography at six months. Two blinded reviewers classified the patency with 98% concordance. A third reviewer adjudicates any discordance. At 6 months urinary TX-M was also measured along with platelet aggregometry. Details of the original studies and principle findings have been reported in previous studies (Gluckman et al., 2011, J. Am. Coll. Cardiol. 57:1069-1077; Gluckman et al., 2009, J. Thromb. Haemost. 7:1457-1464).

Statistical Analysis

All data were expressed as mean±standard error. One-way analysis of variance, followed by Newman-Keuls multiple comparison test, was used to assess the difference between the mean values of different groups within the same study. A difference of $P<0.05$ was considered as significant. For the clinical studies where results were not a normal distribution, median and interquartile range (IQR, Q1-Q3) were presented graphically. Non-parametric analysis (Mann Whitney test) was performed. A difference of $P<0.05$ was considered as significant.

Example 1

Thromboxane Biosynthesis In Vivo in Diabetics vs. Non Diabetics

Hyperactive platelets and abnormal thrombus formation may be a critical component in the development of diabetic micro- and macro-vascular disease. In the following studies, the relationship between glucose, $TXB_2$ generation and platelet activation in human platelets was systematically investigated, and thromboxane levels in diabetic patients with and without thrombosis were analyzed. In addition to highlighting the importance of glucose regulation of platelet activity through $TXA_2$ generation and release, the study identified platelet aldose reductase as a key transducer of plasma glucose in regulating platelet activity.

Figure 1:
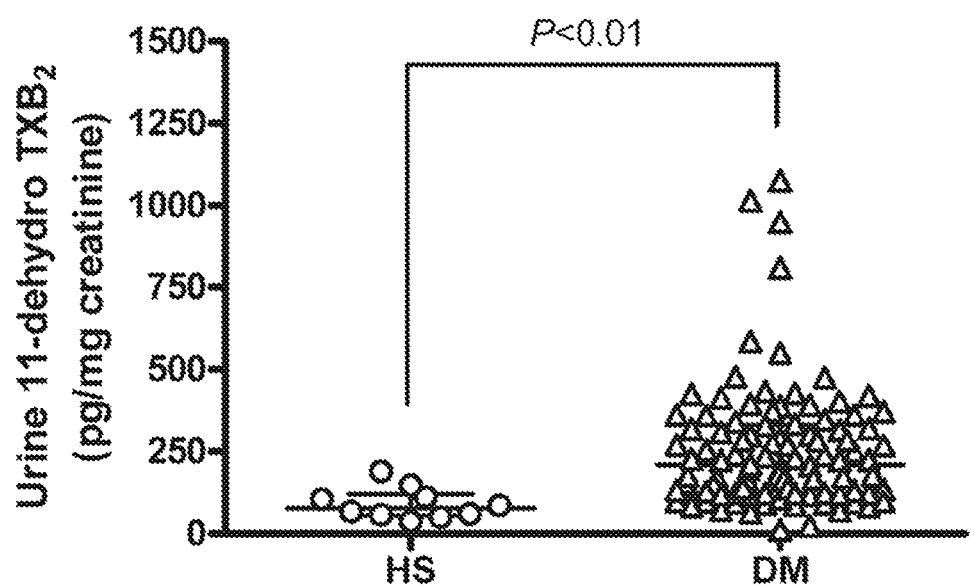
FIG. 1 is a graph illustrating the level of urinary thromboxane metabolite in healthy subjects (HS) and diabetic (DM) patients, with all subjects on low-dose aspirin (100 mg/day). The level of urinary thromboxane metabolite ($TXB_2$) was measured as an index of thromboxane release in HS (n=10) and DM (n=102) patients. Data are expressed as median with interquartile range. A difference of $P<0.05$ was considered as significant.

As illustrated in FIG. 1, there was increased $TXA_2$ generation in vivo (as measured by a major urinary TX metabolite, TX-M) in patients with diabetes mellitus. TX-M was examined in diabetic patients (n=102) and compared to a small group of normal volunteers (healthy subjects, HS; n=10), with all subjects on low-dose aspirin (selective cyclooxygenase (COX)-1 inhibition reducing $TXA_2$ generation for preventing cardiovascular events (Marcus et al., 2002, N. Engl. J. Med. 347:1025-1026)). There was a clear statistically significant increase for the HS group compared to the DM group: the median and IQR (Q1-Q3) was 77.5 pg/mL creatinine (54.0 to 130.0) for HS, 208.8 pg/mL creatinine (123.4 to 330.7) for DM. The mechanism for glucose-induced signaling on platelet TXB2 generation and activation was then analyzed.

Example 2

Figure 2C:
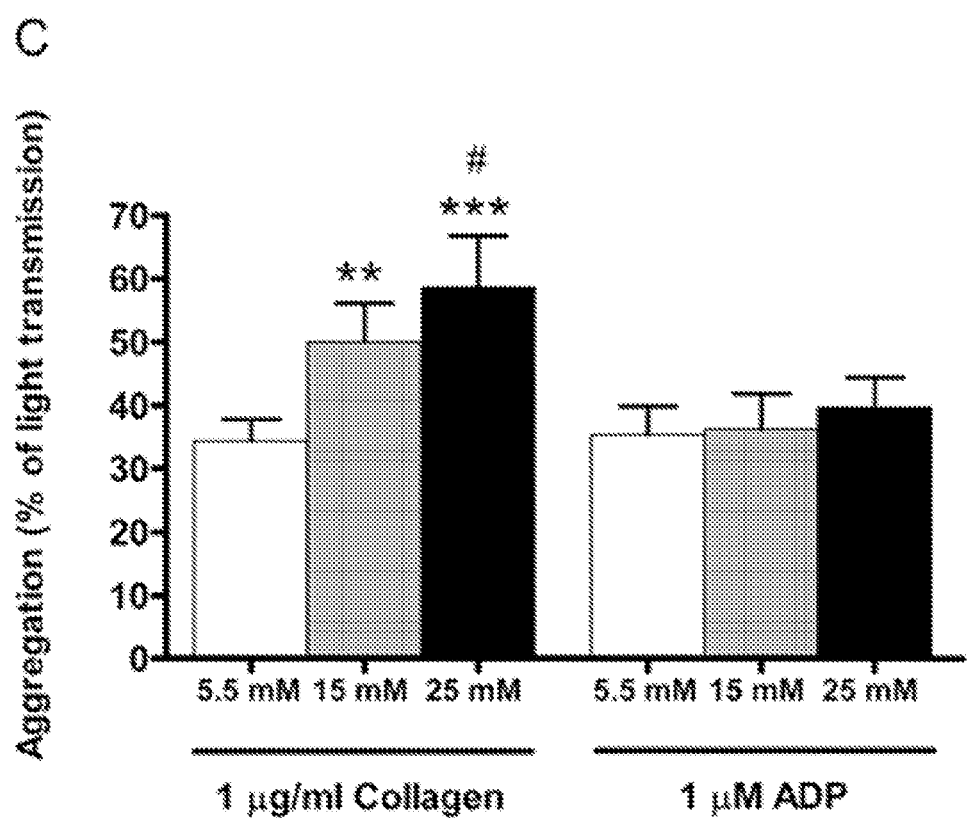
Figures 2D, 2E, 2F:
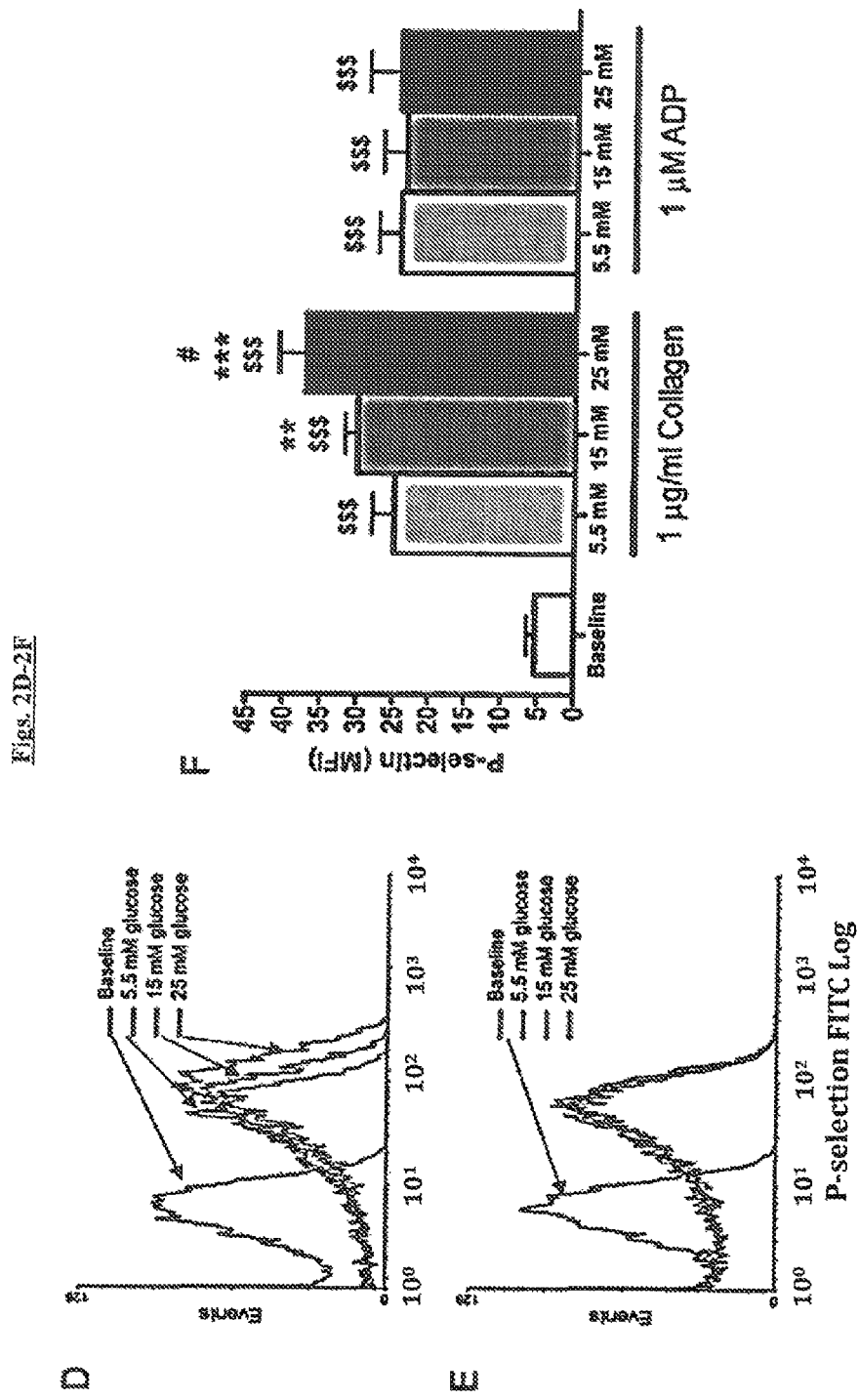

Human Platelet Aggregation and Activation are Exquisitely Sensitive to Glucose Concentrations The effects of glucose on activation were studied in platelets isolated from venous blood of healthy subjects. The aggregation induced by 1 µg/mL collagen was increased when platelets were pre-incubated with increasing concentrations of glucose (FIGS. 2A & 2C). Interestingly, there was no effect of glucose on ADP-induced aggregation (FIGS. 2B & 2C), as measured by percent of light transmission. To further validate this observation, flow cytometry was performed using P-selectin antibodies and a similar dose dependent effect of glucose on platelet activation was observed in response to collagen but not ADP (FIGS. 2D, 2E & 2F). This highlights a sensitivity of human platelets to incremental doses of glucose (5.5-25 mmol/L) when stimulated by collagen. Important questions remained as to the mechanism and how this relates to the initial clinical observations of increased TX-M in diabetic patients despite the use of aspirin (FIG. 1). Interestingly, a recent study using two-dimensional difference gel electrophoresis and mass spectrometry demonstrated that AR expression and its activity contribute to the human platelet activation after stimulation of the GPVI receptor by collagen (Schulz et al., 2010, Blood 115:4102-4110). AR is known to metabolize glucose to sorbitol. The contribution of AR to collagen-induced platelet aggregation was therefore examined.

Example 3

Figures 3A, 3B:
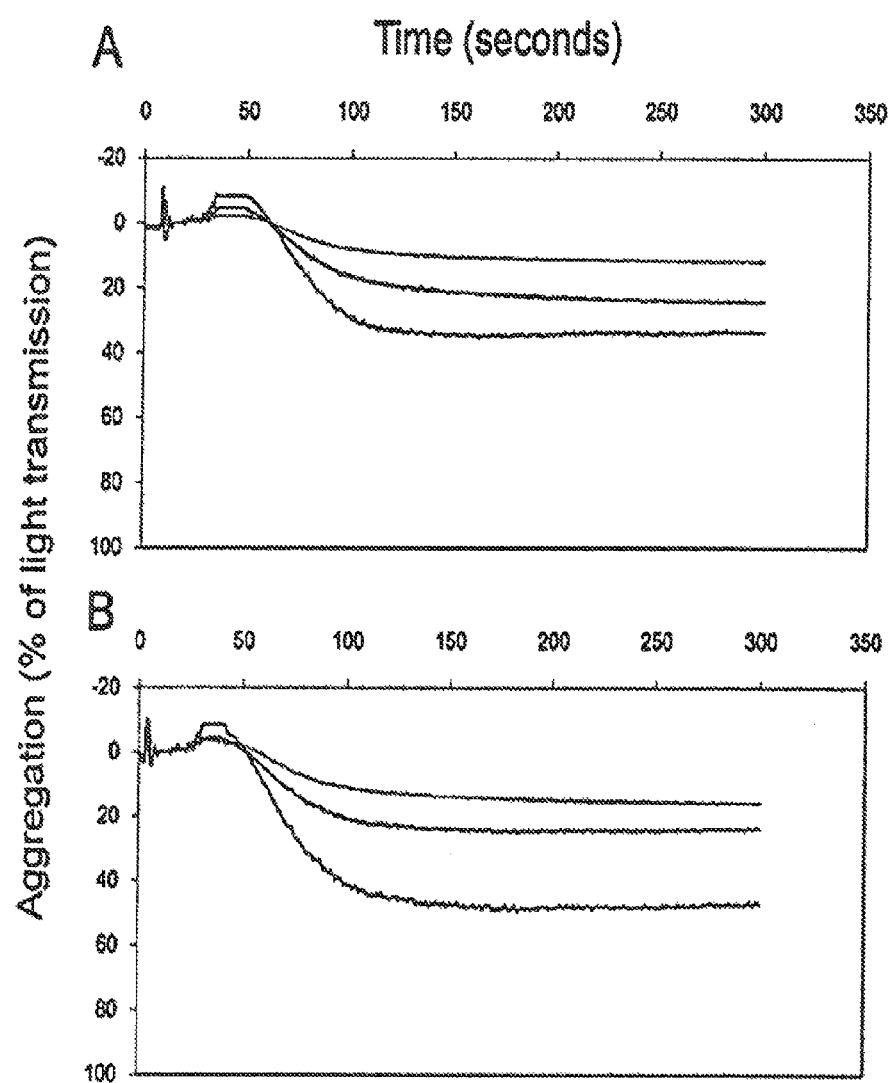
FIGS. 3A-3F, illustrates the finding that AR contributes to the collagen-induced platelet activation and aggregation. Platelet suspensions were incubated with 5.5 mmol/L glucose (NG) or 25 mmol/L glucose (HG) for 90 min in the presence or absence of 1 µmol/L or 10 µmol/L epalrestat (ARI). The percentage of light transmission was measured in platelet suspensions under (FIG. 3A) NG or (FIG. 3B) HG condition in response to 1 µg/mL collagen for 5 min (n=5 healthy subjects).
Figure 3C:
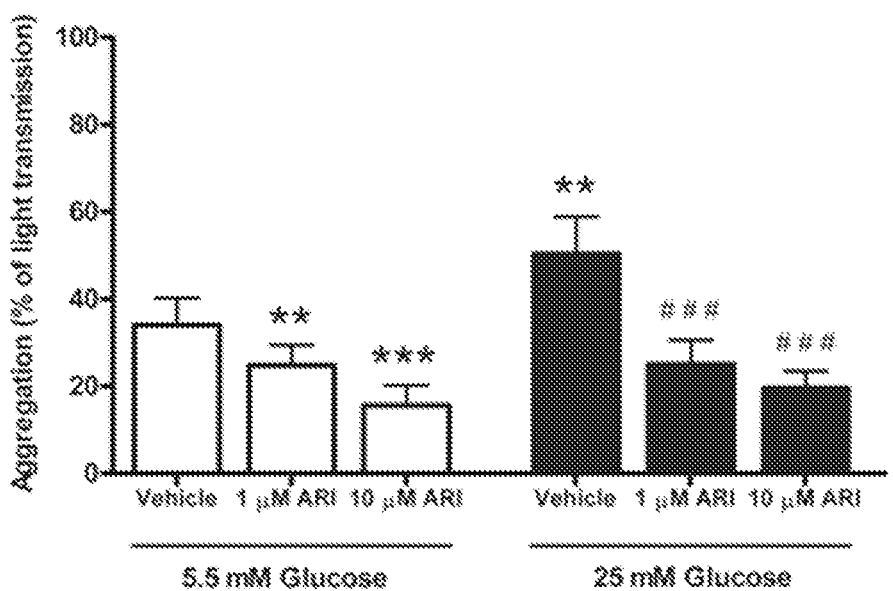
Figure 3D:
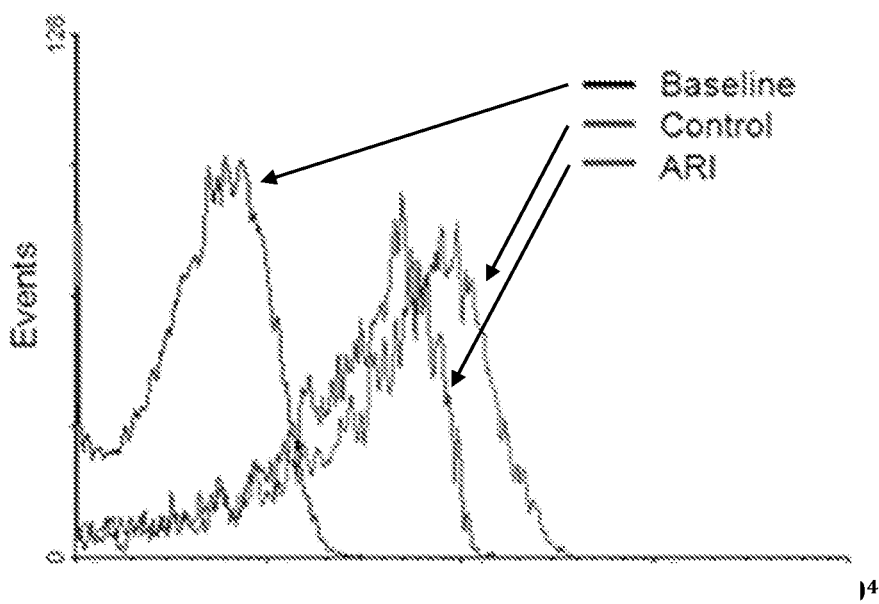
Figures 3E, 3F:
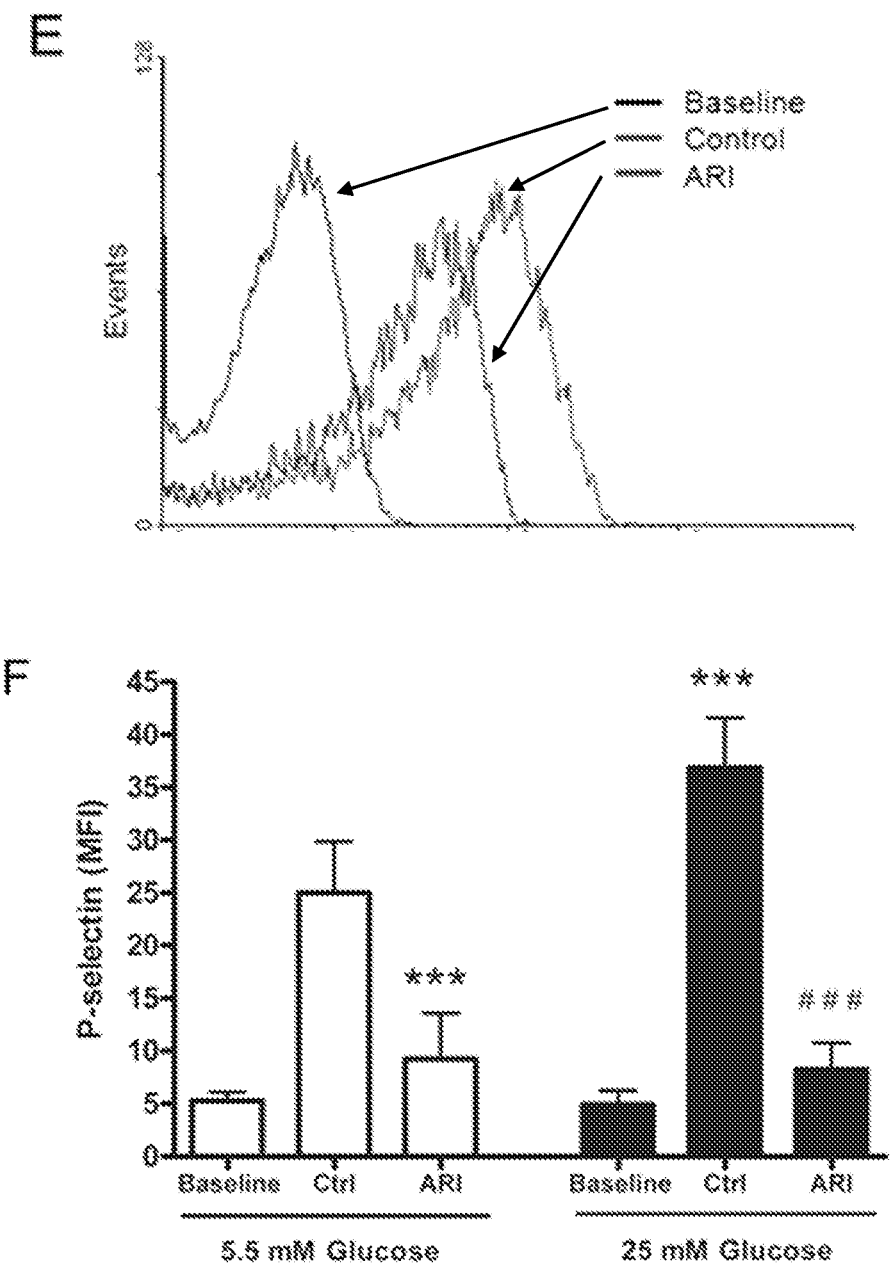
Figure 4:
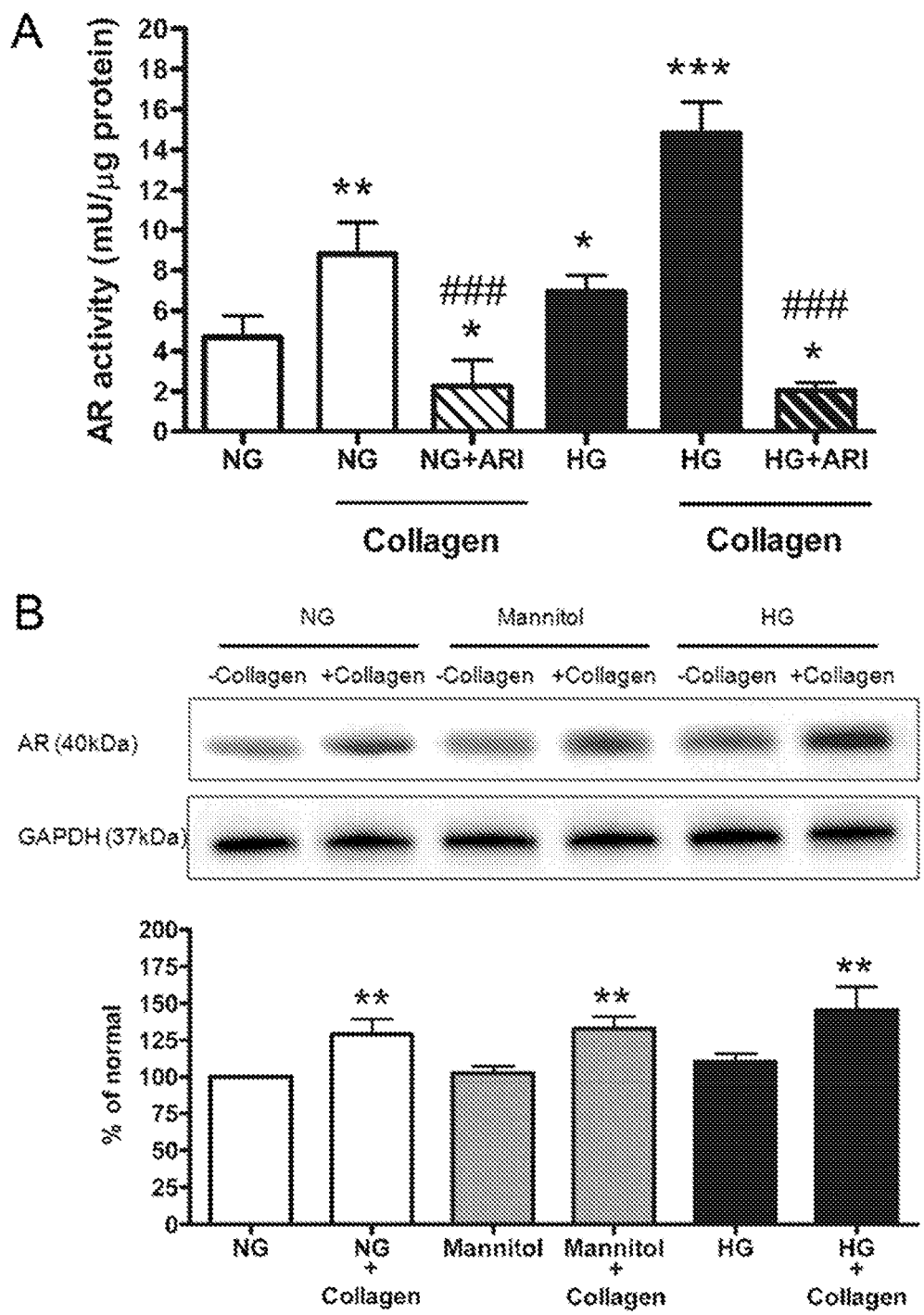
FIG. 4, comprising
Figure 14:
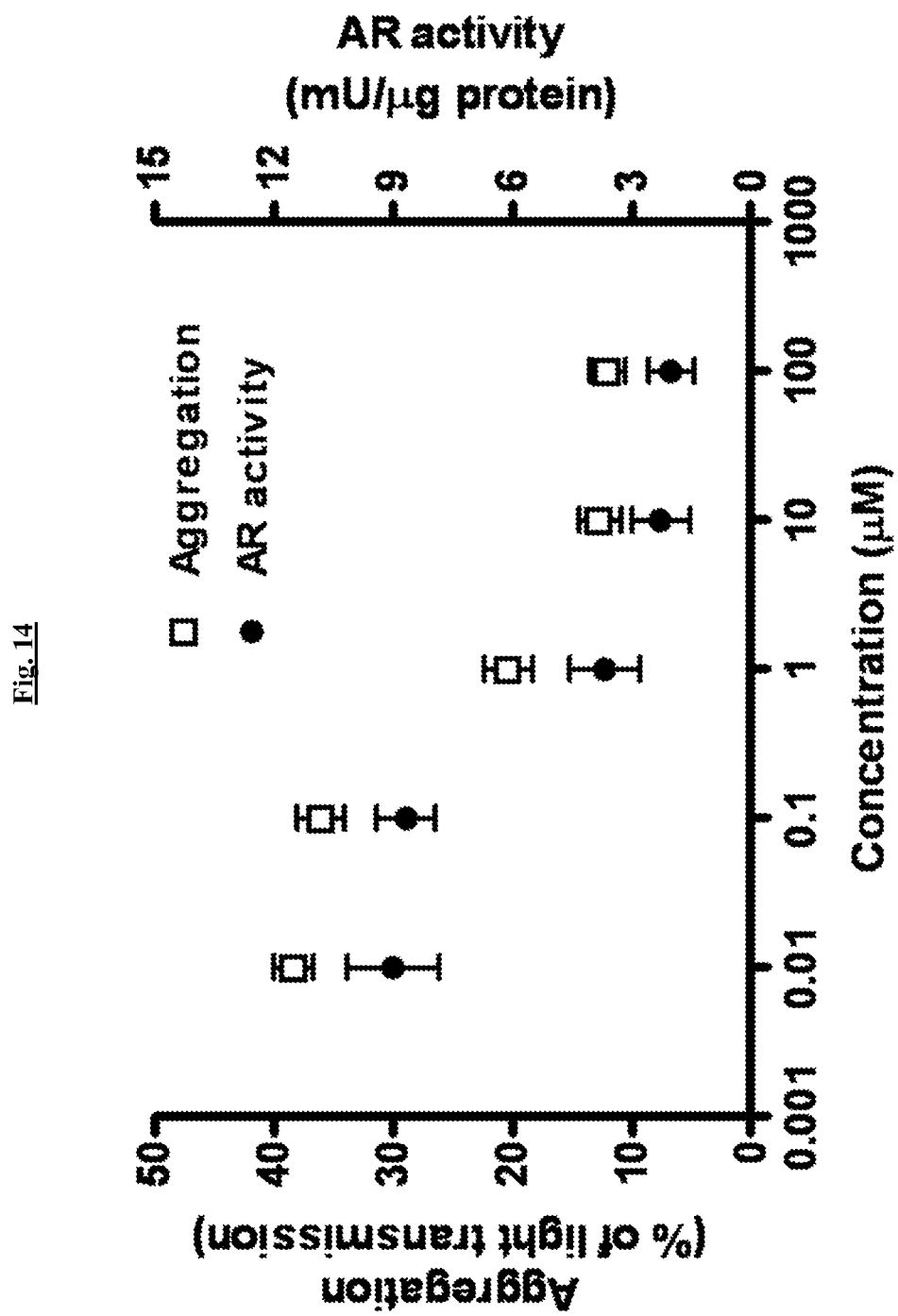
FIG. 14 is a graph illustrating the dose response of epalrestat on collagen-induced aggregation AR activity in human platelets. Platelet suspensions were incubated with NG for 90 min in the presence or absence of different concentrations of epalrestat (0.01-100 µmol/L), prior to stimulation by 1 µg/mL collagen for 10 min. Data are expressed as mean±SE (n=5 healthy subjects).
Figure 15A:
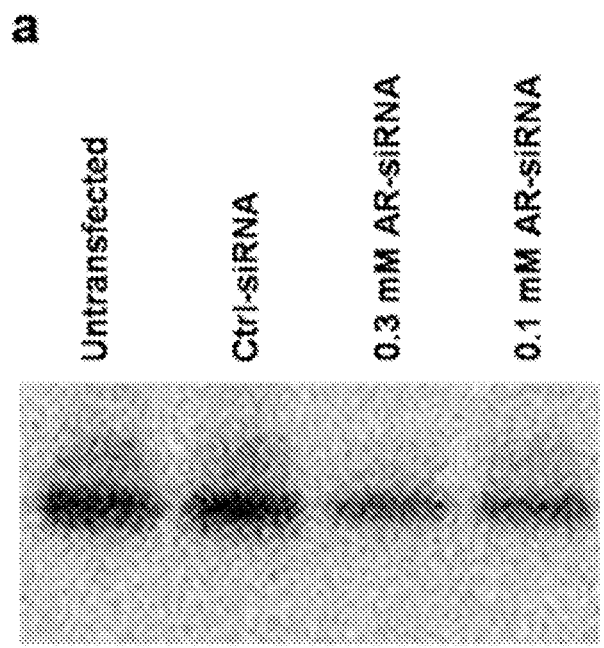
FIGS. 15A-15C, illustrates the finding that silencing of AR reduces the P-selectin translocation to membrane in megakaryocytes (MEG-01) culture. The MEG-01 cells were transfected with 0.1 or 0.3 mM AR siRNA. After 48 hour NG incubation, the P-selectin translocation to membrane was assessed by flow cytometry in response to 1 µg/mL collagen.
Figures 15B, 15C:
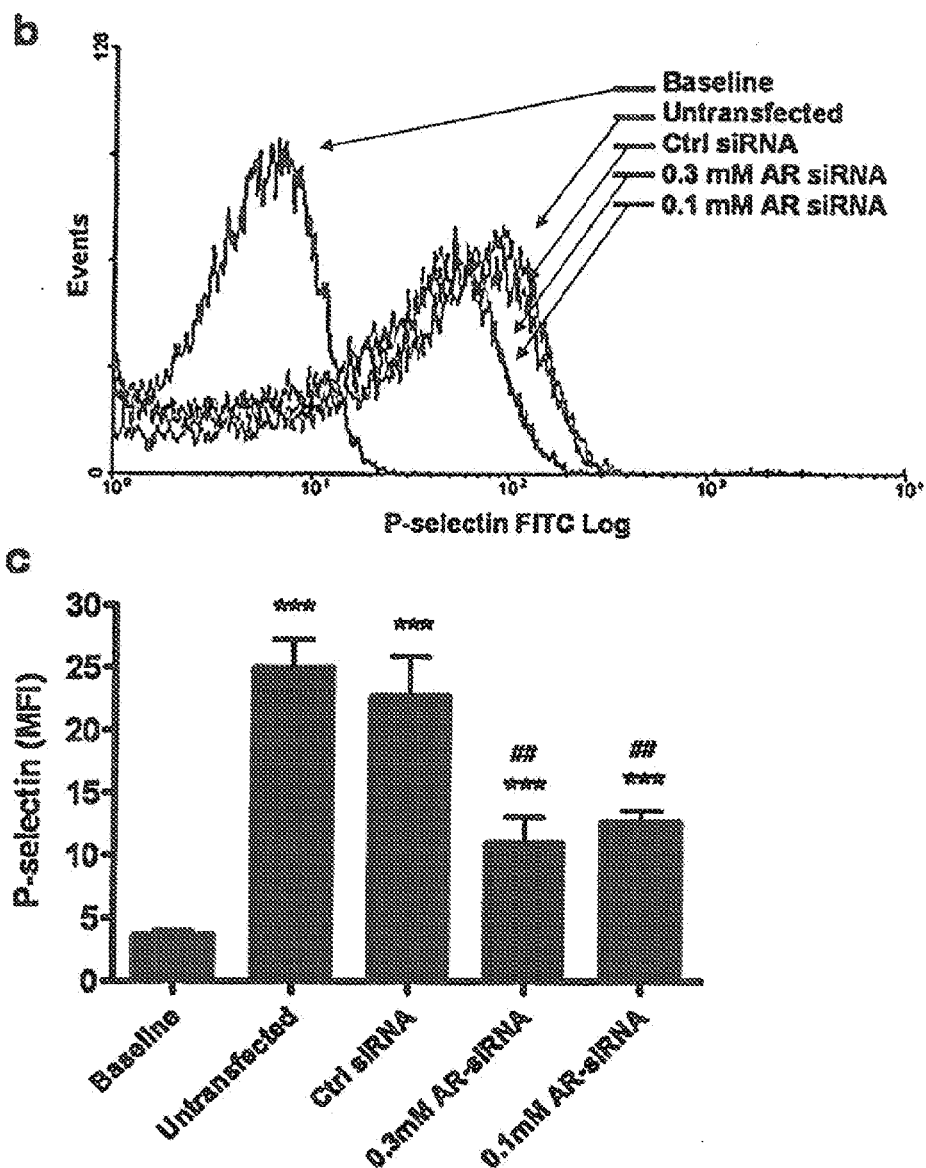

AR Contributes to Collagen-Induced Platelet Aggregation Under Normal and High Glucose Conditions The effect of 5.5 or 25 mmol/L glucose (basal or hyperglycemia) was tested on human platelets in the presence or absence of epalrestat (selective aldose reductase inhibitor). As shown in FIG. 3, glucose again potentiated the collagen-stimulated aggregation in human platelets. In response to 1 µg/mL collagen, the aggregation in 25 mmol/L glucose was 25% higher than that in 5.5 mmol/L glucose, and was attenuated by treatment with 1-10 µmol/L epalrestat (FIG. 3A-C), suggesting that such aggregation was abolished by inhibition of AR. The concentration of epalrestat used in the present study was based on the dose response curve (FIG. 14). To corroborate the spectrophotometric aggregation assays, P-selectin, the marker for platelet activation, was analyzed using flow cytometry. As in FIG. 2F, collagen-induced P-selectin surface expression was enhanced in HG compared to NG (FIG. 3D-3F), and epalrestat effectively attenuated the increase in P-selectin. In addition, genetic knockdown of AR reduced the P-selectin translocation to membrane in the collagen-stimulated megakaryocyte (MEG-01) platelet-like particles in NG (FIG. 15). These results combined suggest that AR plays a central role in the collagen-induced platelet aggregation under NG, but particularly under HG conditions. Supporting this data HG alone, or collagen treatment in NG, increased AR activity, and that the combination of collagen and HG potentiated this effect (FIG. 4A). This increase in activity could not be accounted for by increased AR expression as collagen treatment (in NG or HG but not HG alone) induced only a modest increase in AR expression (FIG. 4B) which did not correlate with the degree of activation (FIG. 4A). Thus collagen and high glucose synergize in activating AR.

Example 4

Figures 5A, 5B:
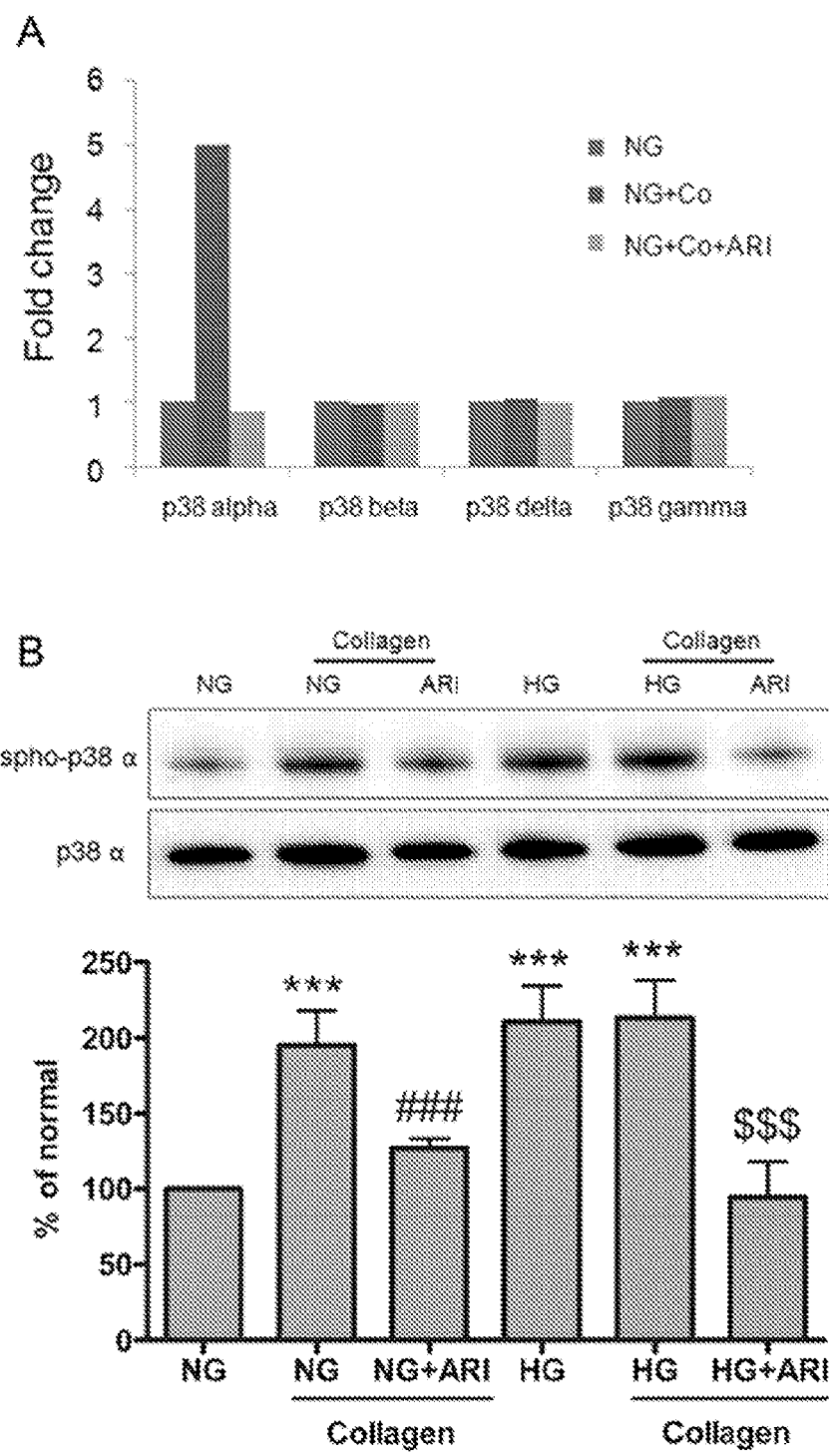
FIGS. 5A-5C, illustrates the finding that AR is required for p38α MAPK phosphorylation in collagen-stimulated platelets. Platelet suspensions were incubated with NG or HG for 90 min in the presence and absence of 10 µmol/L epalrestat (ARI), prior to stimulation by 1 µg/mL collagen for 10 min, and the total extract was harvested for experiments.
Figure 5C:
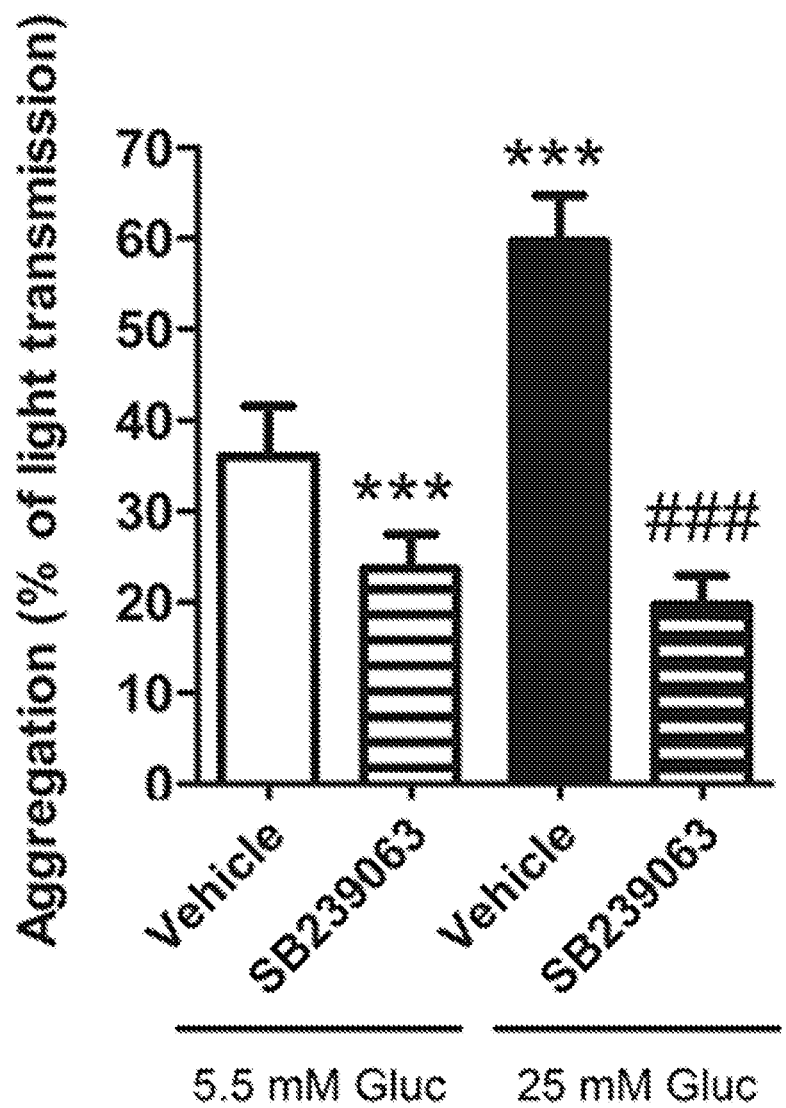

Inhibition of AR Attenuates the Phosphorylation of p38α MAPK in Human Platelets in Response to Collagen Under Normal and High Glucose Conditions In order to identify potential signaling mechanisms by which AR enhances collagen-induced platelet aggregation, a screen was performed using a phospho-proteomic-kinase array (R & D Systems). Human platelets induced by 1 μg/mL collagen exhibited a five-fold increase in p38α phosphorylation which was markedly attenuated by 10 μmol/L epalrestat. A p38 phosphoproteomic array confirmed that collagen specifically induced phosphorylation of the alpha isoforms (FIG. 5A). The p38α activation by collagen and inhibition by epalrestat in both NG and HG was confirmed by Western blot (FIG. 5B). Interestingly, p38α phosphorylation was significantly increased in HG-incubated platelets even in the absence of collagen stimulation (FIG. 5B), suggesting that HG incubation may potentiate platelet aggregation via p38α, perhaps through its downstream effector cytosolic phospholipase $A_2$ ($cPLA_2$) (Kramer et al., 1996, J. Biol. Chem. 271: 27723-27729), leading to thromboxane production. Most importantly, collagen-induced platelet aggregation in both NG and HG was reduced by pretreatment with a p38 inhibitor (FIG. 5C).

Figure 6B:
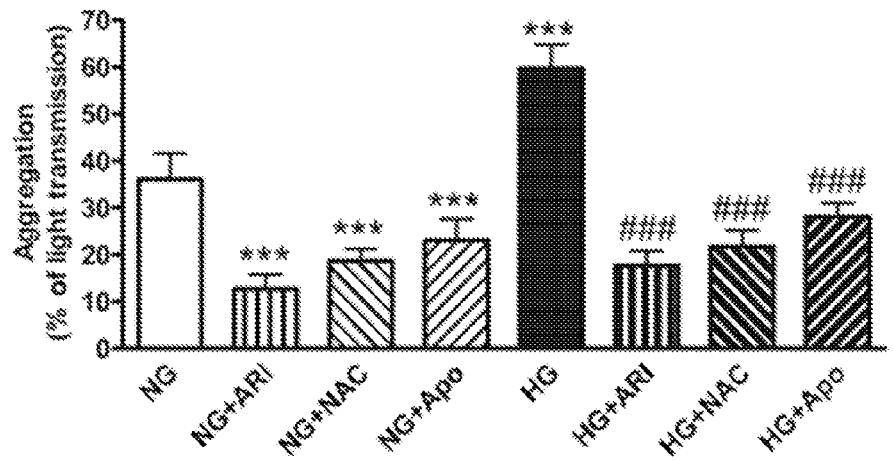
Figure 6C:
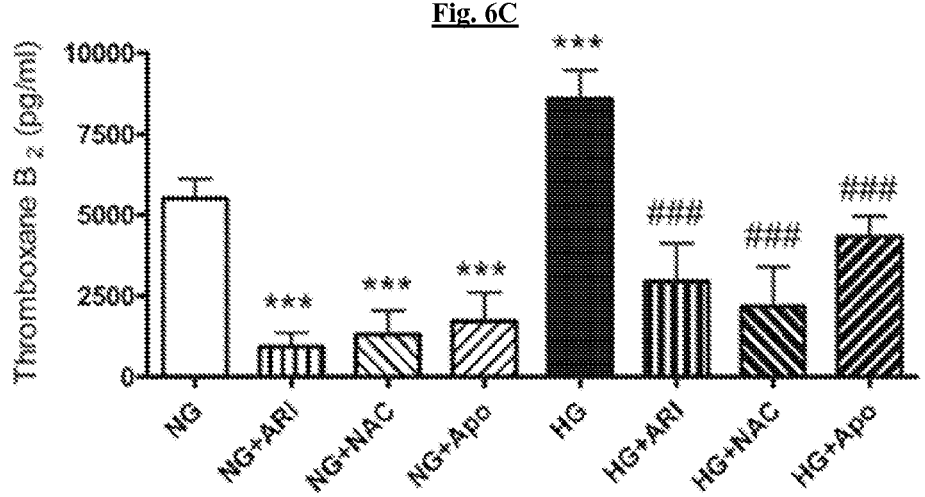

The mechanism by which collagen activates p38α was then probed. Collagen activates AR (FIG. 4A). As AR can lead to ROS generation, which can regulate p38 (Coulon et al., 2003, Free Radic. Biol. Med. 35:616-625), oxidative stress production was measured by using specific fluorescent probes. The level of oxidative stress and superoxide was significantly increased upon collagen-induced platelet aggregation, and was even higher in the HG compared to NG (FIG. 6A). The increases were significantly attenuated by epalrestat, suggesting that AR contributes to oxidative stress in the collagen-stimulated platelets. Treatment with 10 mmol/L NAC (ROS scavenger) or 100 μmol/L apocynin (NAD(P)H oxidase inhibitor) also significantly reduced the level of oxidative stress and superoxide. Moreover, HG increased the oxidative stress and superoxide production even in the absence of collagen. Notably, NAC and apocynin attenuated the collagen-induced platelet aggregation to a similar extent as ARI, indicating that the oxidative stress likely transduced the AR signal (FIGS. 6B & 6C).

Figure 7A:
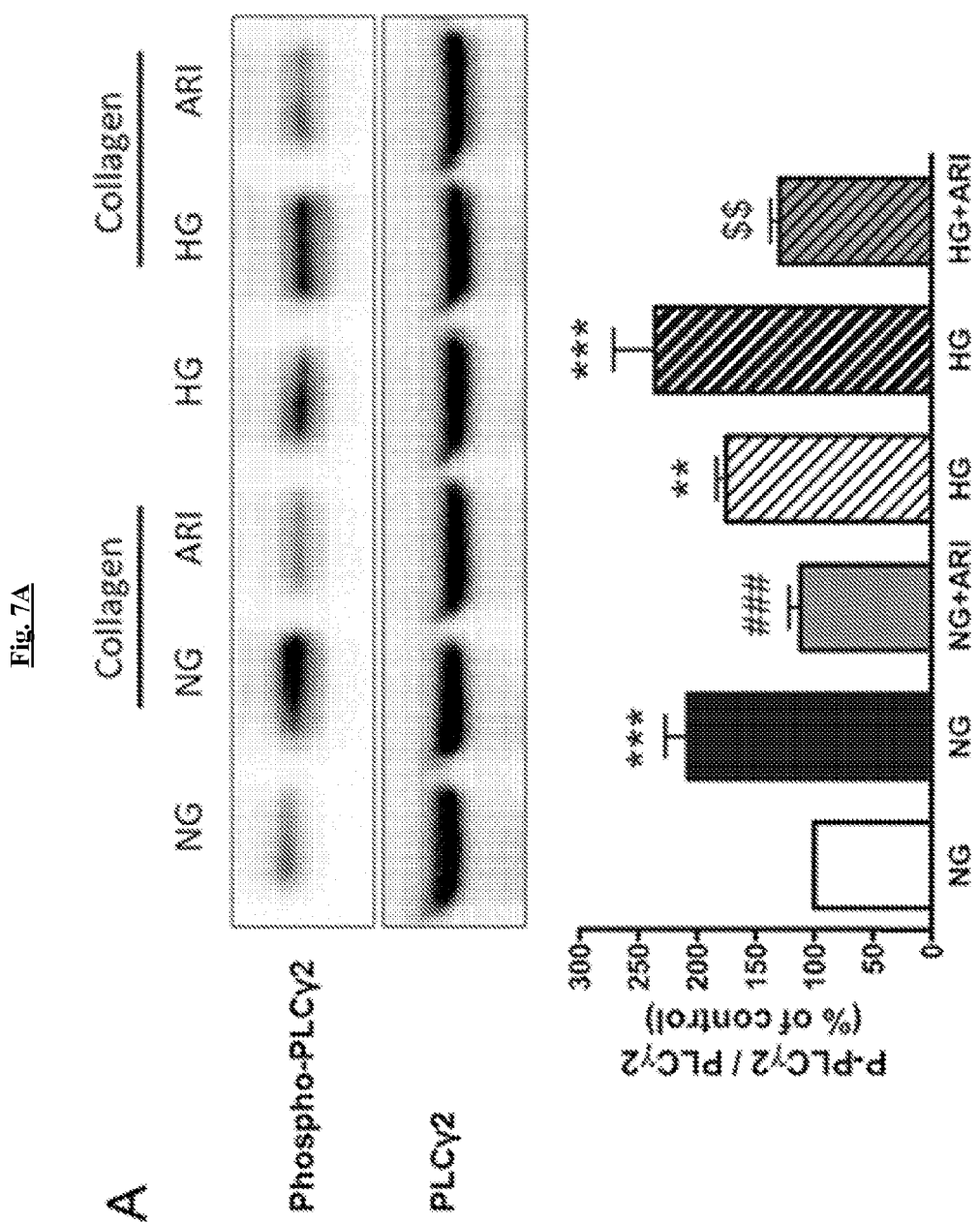
FIGS. 7A-7B, illustrate the finding that AR is required for PLC phosphorylation in collagen-stimulated platelets.
Figure 7B:
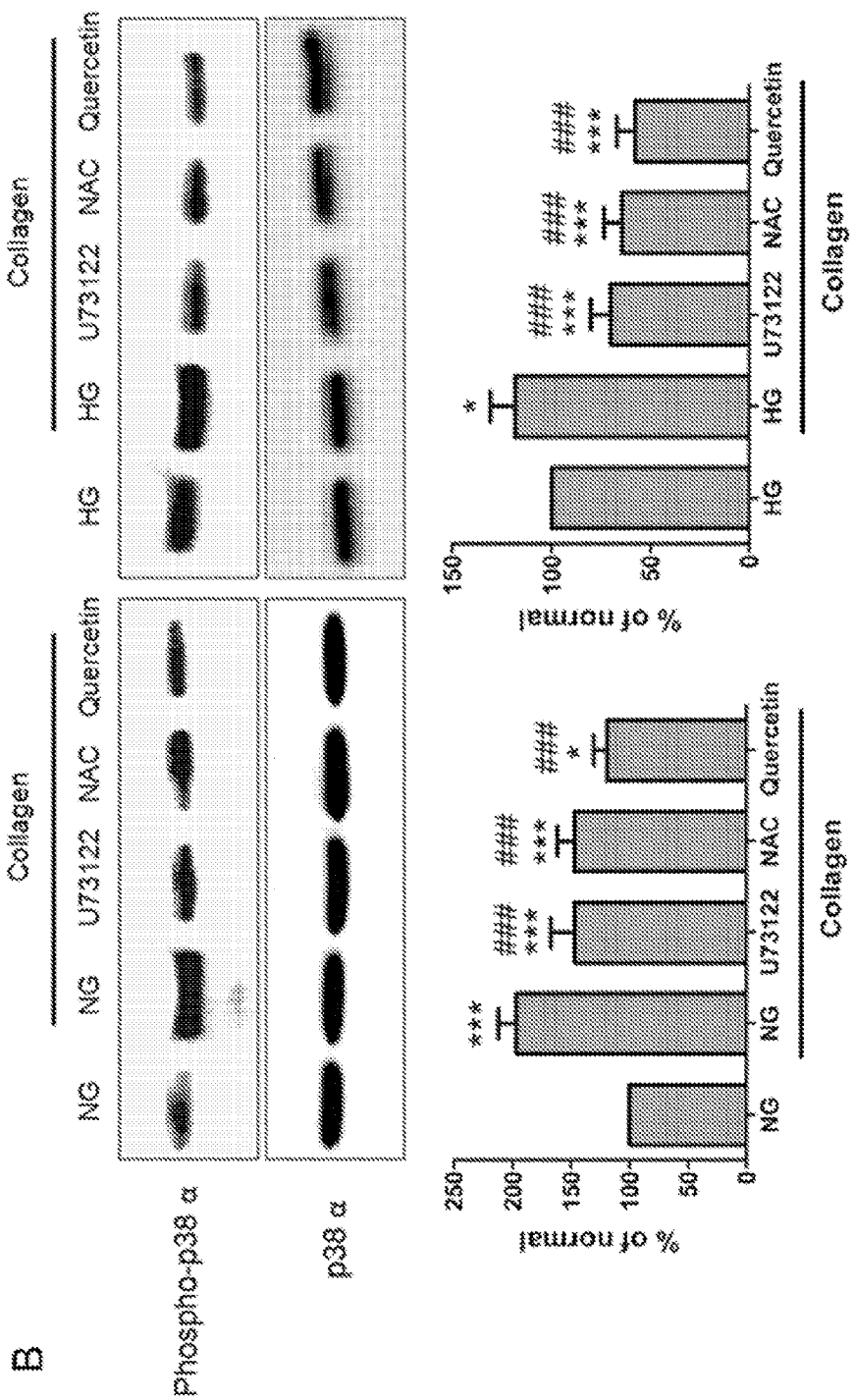

PLC-γ1 & 2 are phosphorylated and activated in response to oxidative stress (Wang et al., 2001, J. Biol. Chem. 276: 28364-28371; Leoncini et al., 2007, J. Cell Biochem. 100: 1255-1265), and are thought to play an important role in platelet activation (Leoncini et al., 2007, J. Cell Biochem. 100:1255-1265). As shown in FIG. 7A, under both NG and HG conditions, the phosphorylation of PLC-γ2, but not PLC-γ1, was significantly enhanced upon the collagen-induced platelet aggregation. Moreover, PLC-γ2 phosphorylation was increased under HG condition even without collagen stimulation. As shown in FIG. 7B, treatment with the PLC inhibitor U73122 or the ROS scavenger NAC significantly reduced the collagen-induced phosphorylation of p38α MAPK, providing evidence that p38α MAPK activation was regulated by PLC-γ2 during collagen-induced platelet aggregation, and this process is associated with oxidative stress. In addition, treatment with quercetin (an ARI inhibitor with broad specificity and structurally distinct from epalrestat) also attenuated the collagen-induced phosphorylation of p38α MAPK, further confirming the effect of AR inhibition (FIG. 7B). Taken together, these results suggest that AR contributes to the collagen-induced platelet activation via oxidative stress-induced tyrosine phosphorylation of PLC-γ2.

Example 5

Figures 8B, 8C, 8D:
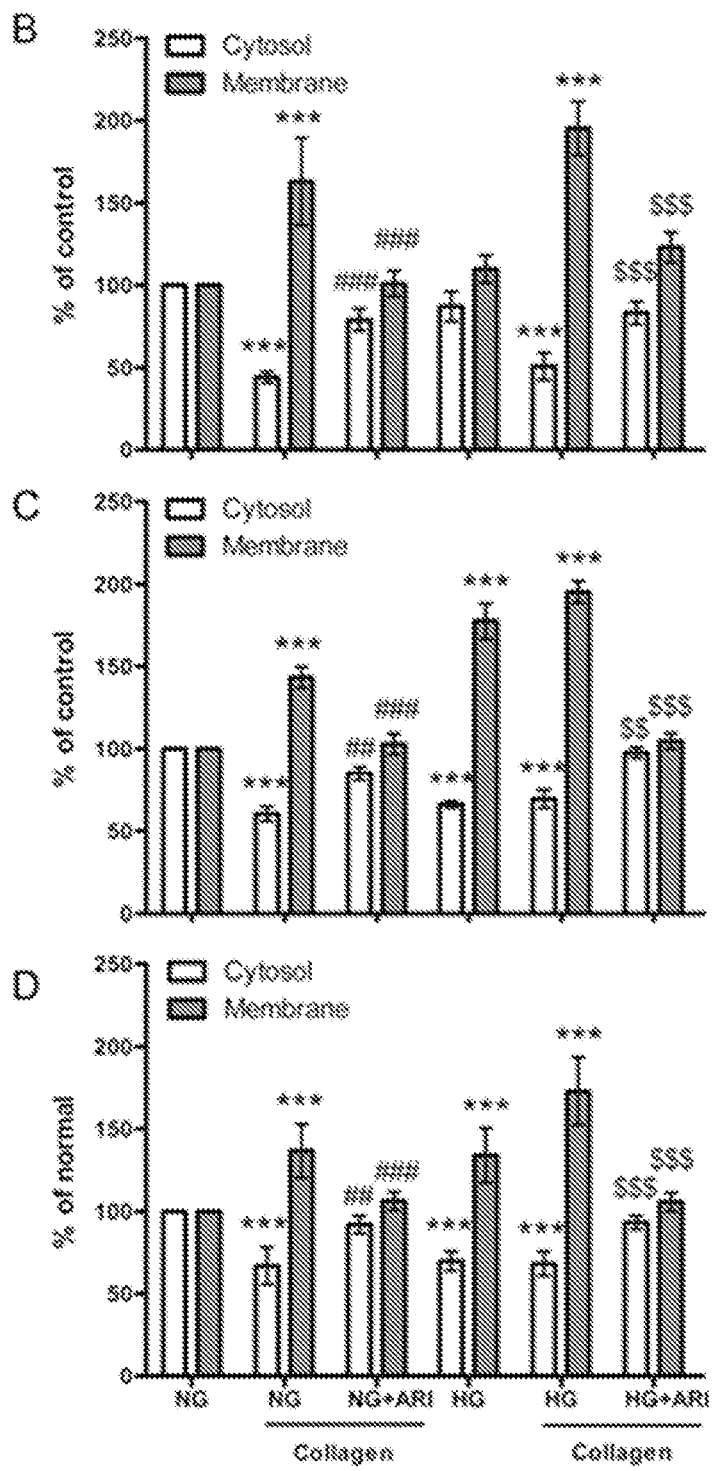
Figure 9A:
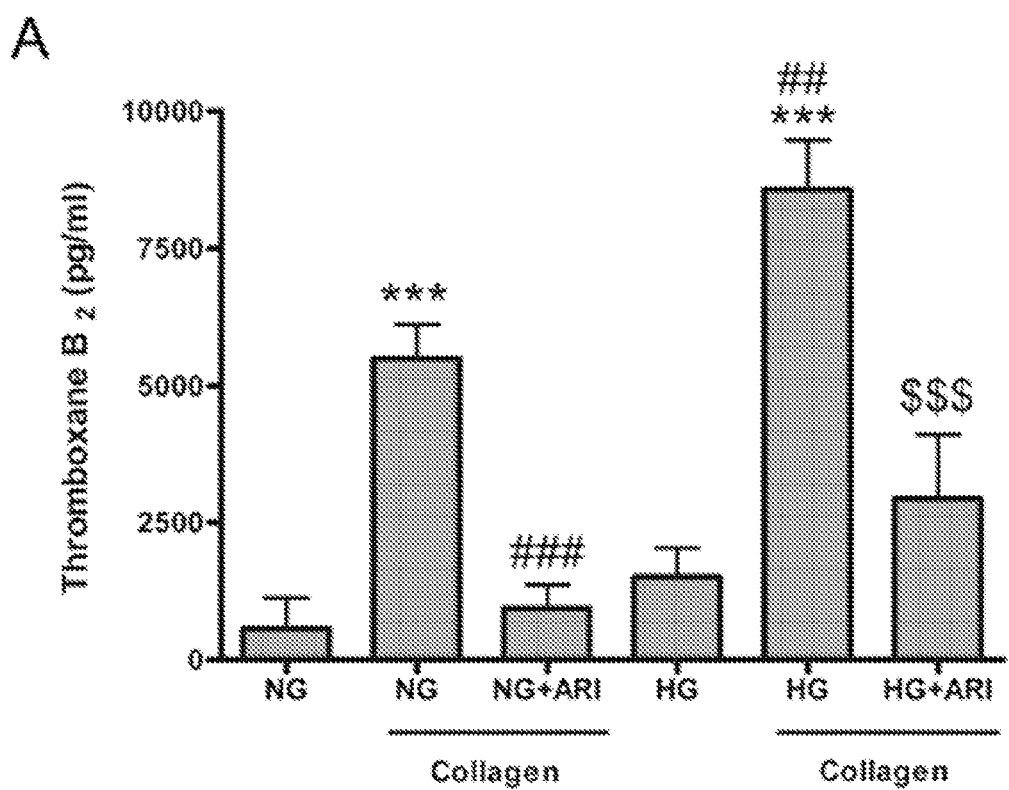
FIGS. 9A-9C, illustrates the finding that AR is involved in thromboxane signaling in platelets: Role of AR in (FIG. 9A) thromboxane generation and (FIG. 9B) surface expression of thromboxane receptor in collagen-stimulated platelets. Platelet suspensions were incubated with NG or HG for 90 min in the presence and absence of 10 μmol/L epalrestat, prior to stimulation by 1 μg/mL collagen for 10 min. The level of TX was assayed in the supernatant. The expression of TX receptor was assessed in the membrane and cytosolic fractions. Data are expressed as mean±SE (n=5 healthy subjects). *P<0.001 compared with values incubated in NG alone; $^{\#\#\#}$P<0.001 & $^{\#\#}$P<0.01 compared with values in NG with the addition of 1 μg/mL collagen; $^{\$\$\$}$P<0.01 & $^{\$\$}$P<0.01 compared with values in HG with the addition of 1 μg/mL collagen.
Figure 9B:
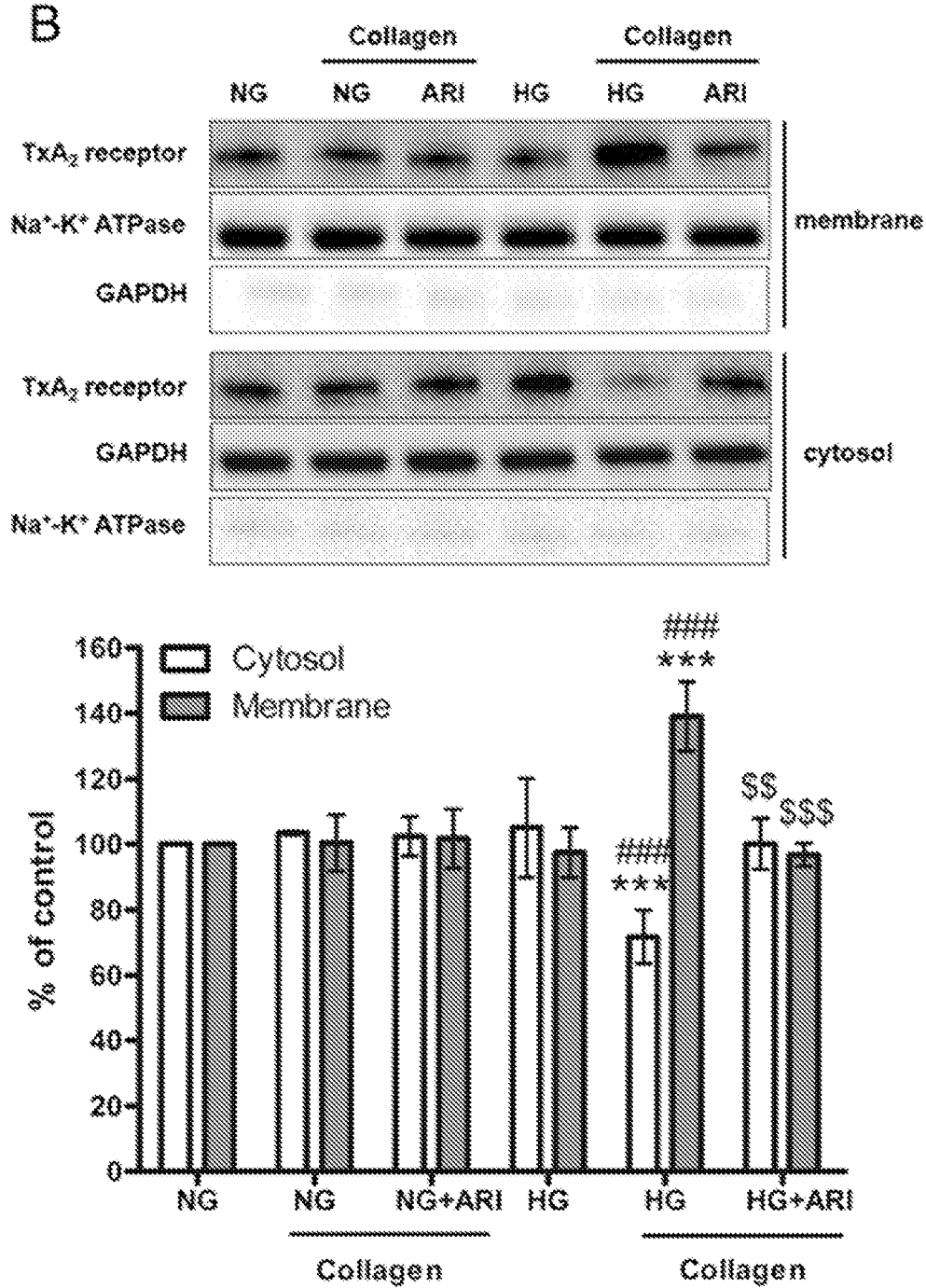
Figures 16B, 16C, 16D:
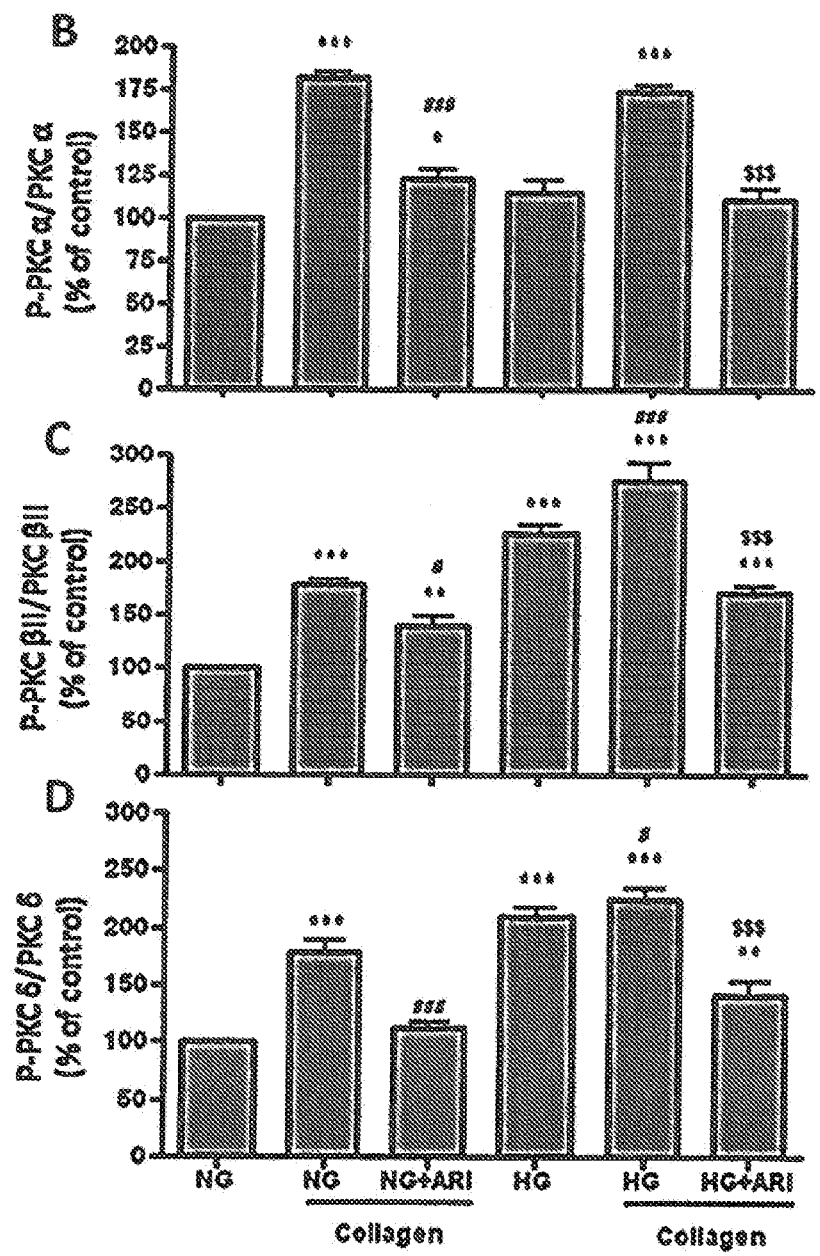

Inhibition of AR Prevents the Translocation and Phosphorylation of PKC Isoforms (α, βII & δ) in Human Platelets in Response to Collagen Under Normal and High Glucose Conditions PLCγ leads to the generation of DAG, which activates the PKC isoforms (Lee & Severson, 1994, Am. J. Physiol. 267: C659-678; Mellor & Parker, 1998, Biochem J. 332 (Pt 2):281-292; Nishizuka, 1992, Science 258:607-614). p38α MAPK is the activated downstream of PKC in platelets (Morton et al., 1989, Biochem J. 258:157-163; Santoro et al., 1991, Cell Regul. 2:905-913; Nadal-Wollbold et al., 2002, FEBS Lett. 531:475-482; Saklatvala et al., 1996, J. Biol. Chem. 271:6586-6589; Papkoff et al., 1994, Mol. Cell. Biol. 14:463-472). The effect of AR on PKC isoforms (α, βII & δ) known to be present in platelets was studied. As shown in FIGS. 8A & 8B, PKC-α was highly expressed in the cytosolic fraction in the human platelets under both NG and HG conditions. Upon collagen stimulation, the level of PKC-α was increased in the membrane compared to the cytosolic fraction, indicating PKC-α translocation to a membrane during platelet aggregation. Inhibition of AR with 10 μmol/L epalrestat prevented the collagen-induced translocation of PKC-α under both NG and HG conditions. Similar to PKC-α, PKC-βII & δ were highly expressed in the cytosolic fraction and translocate to the membrane upon collagen-induced platelet aggregation under NG condition (FIGS. 8A, 8C & 8D). However, under HG condition, the levels of PKC-βII & δ were higher in the membrane fraction than in the cytosolic fraction with or without 1 μg/mL collagen, which was attenuated by the treatment with 10 μmol/L epalrestat. The blots were probed with the antibodies against $Na^+/K^+$ ATPase and GAPDH, which served as the membrane and cytosolic markers respectively (FIG. 9B). Since the subcellular translocation of PKC-α, βII & δ were prevented by AR inhibitor, it was next measured whether inhibition of AR prevents the phosphorylation of PKC-α, βII & δ by using phospho-specific antibodies which correlate with kinase activity in total extracts. Consistent with the previous genetic knockout and inhibitor studies on the role of PKC isoforms in platelet aggregation (Harper & Poole, 2010, J. Thromb. Haemost. 8:454-462; Yacoub et al., 2006, J. Biol. Chem. 281:30024-30035; Gilio et al., 2010, J. Biol. Chem. 285:23410-23419), the phosphorylation of different PKC isoforms was in line with the findings in their translocation (FIG. 16), indicating that PKC-α, βII & δ translocation from cytoplasm to membrane and phosphorylation are required for collagen-induced aggregation. In addition, these results suggest that HG potentiates the activation of PKC-βII & δ similar to the effect of collagen, in an AR-dependent manner.

Example 6

Figure 9C:
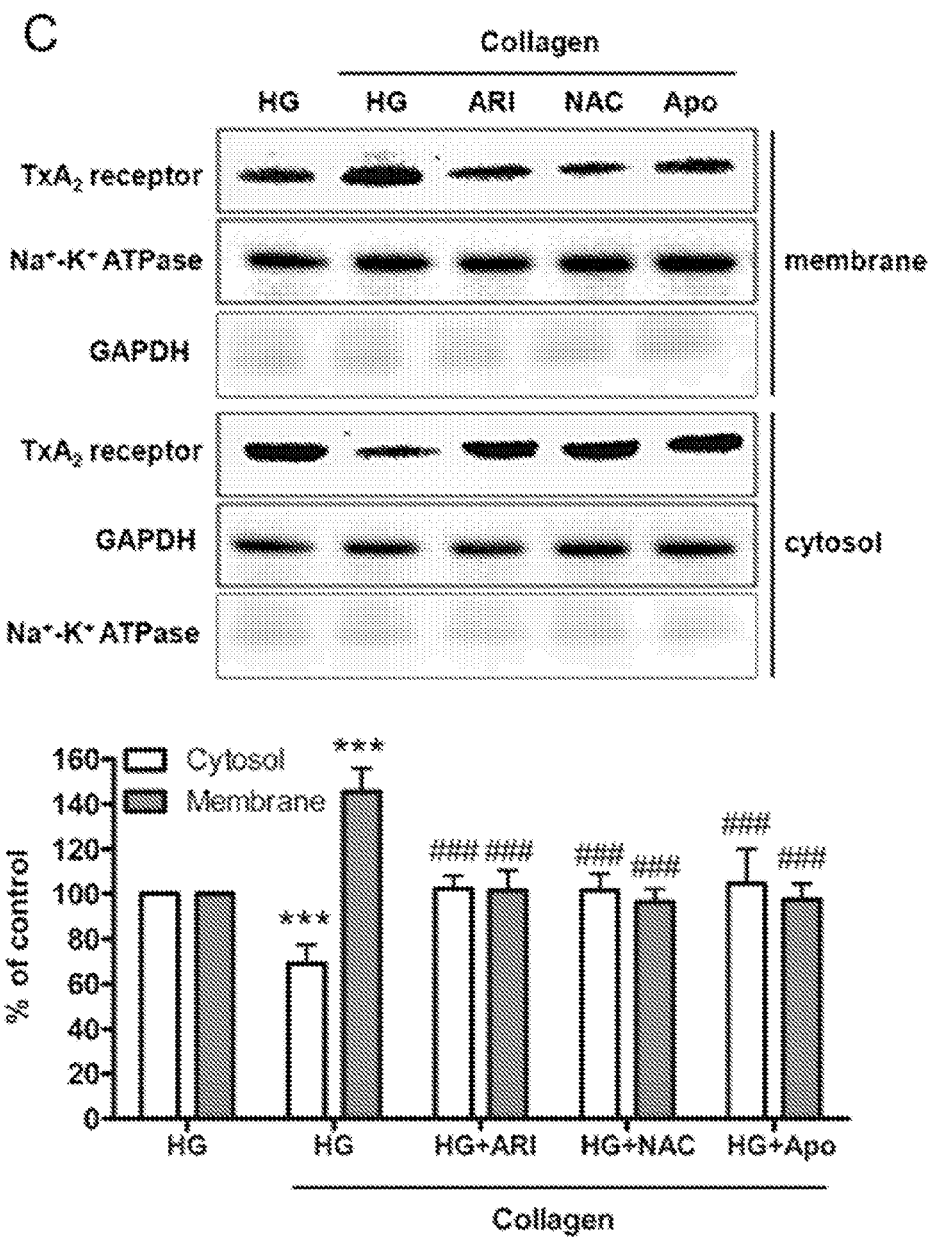

Inhibition of AR Blocks Thromboxane Release in Human Platelets in Response to Collagen Under Normal and High Glucose Conditions Cytosolic phospholipase $A_2$ (cPLA$_2$) generates arachidonic acid, the substrate for prostanoid synthesis. As cPLA$_2$ is a downstream effector of p38α MAPK in platelets (Kramer et al., 1996, J. Biol. Chem. 271:27723-27729; Coulon et al., 2003, Free Radic. Biol. Med. 35:616-625), AR may contribute to collagen-induced aggregation via enhanced TXA$_2$ signaling. The generation of TXB$_2$ and the levels of thromboxane receptor (TP) in the cytosolic and membrane fractions were assessed. During collagen-induced platelet aggregation, TXB$_2$ generation was increased by two-fold (from ~400 to ~800 pg/mL) under NG, and nearly by three-fold (from ~400 to ~1100 pg/mL) in HG (FIG. 9A). TXB$_2$ required AR activity, as treatment with 10 μmol/L epalrestat significantly reduced the level of TXB$_2$ released from platelets. The surface expression of TP was also significantly increased and its expression in the cytosolic fraction was decreased upon the collagen-induced platelet aggregation in HG group but not in NG group (FIG. 9B). Treatment with 10 μmol/L epalrestat significantly abolished the changes in surface expression. ROS also contributed to the TXB$_2$ induction (FIGS. 6A & 6C) and increased platelet activity (FIG. 6B). In addition, the high glucose-induced surface expression of TX receptor was also significantly attenuated by treatment with NAC and apocynin (FIG. 9C) supporting a role for ROS. Collectively, these results suggest that AR and oxidative stress are required for hyperglycemia-induced thromboxane generation and TX receptor surface expression.

Example 7

Correlation of TXB$_2$ Generation with Increased Platelet Aggregation

Figures 10A, 10B:
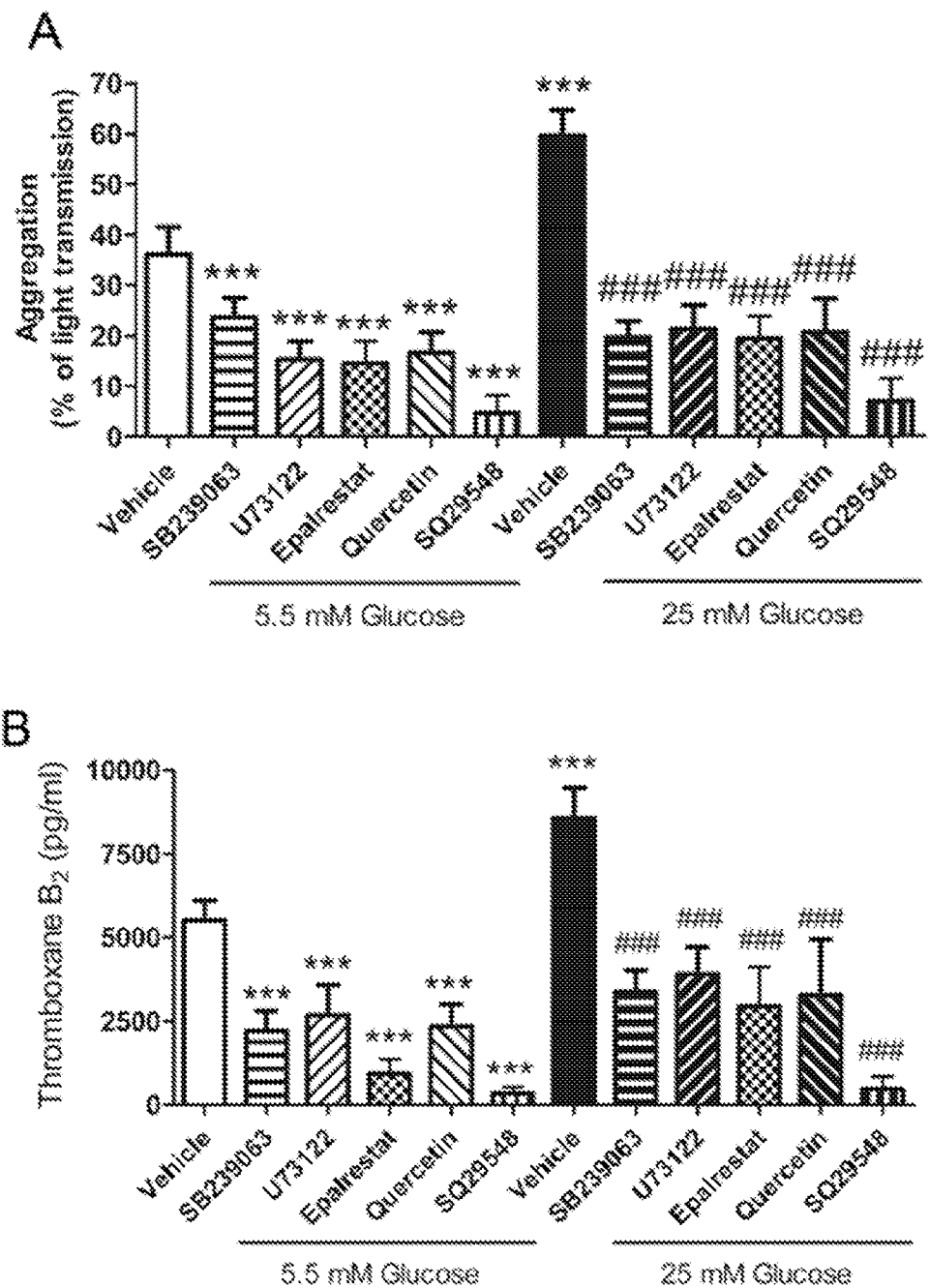
FIGS. 10A-10C, illustrates the finding that activation of p38α MAPK signaling pathway is required for the TX generation and aggregation in collagen-stimulated platelets. Platelet suspensions were incubated with NG or HG for 90 min in the presence or absence of 50 μmol/L SB239063, 5 μmol/L U73122, 10 μmol/L quercetin and 10 μmol/L SQ29548 (1S-[1-alpha,2-beta-(5Z),3-beta,4-alpha]-7-[3-[[2-[(phenylamino)carbonyl]hydrazino]methyl]-7-oxabicyclo[2.2.1]hept-2-yl]-5-heptenoic acid), prior to stimulation by 1 μg/mL collagen.

A pathway in which AR contributes to platelet activation via PLC-dependent activation of p38α with subsequent TXA$_2$ generation was delineated. To validate this pathway, platelet aggregation and TXB$_2$ levels were measured in the presence of U73122 (PLC inhibitor), SB239063 (p38 inhibitor; trans-4-[4-(4-Fluorophenyl)-5-(2-methoxy-4-pyrimidinyl)-1H-imidazol-1-yl]cyclohexanol), quercetin, and SQ29548 (thromboxane receptor antagonist; 1S-[1-alpha,2-beta-(5Z),3-beta,4-alpha]-7-[3-[[2-[(phenylamino)carbonyl]hydrazino]methyl]-7-oxabicyclo[2.2.1]hept-2-yl]-5-heptenoic acid). Treatment with PLC and p38 inhibitors attenuated the collagen-induced TXB$_2$ release, suggesting that PLC-γ2 and its downstream effector, p38α MAPK contributes to TXB$_2$ release. Moreover, all these inhibitors reduced platelet aggregation in response to 1 μg/mL collagen. Importantly, treatment with SQ29548 (thromboxane receptor antagonist) also attenuated the collagen-induced platelet aggregation, suggesting an important role for thromboxane receptor in increasing platelet aggregation in NG or HG (FIG. 10A). SQ29548 also attenuated collagen-induced TXA2 release, suggesting a potential positive feedback mechanism (FIG. 10B). Collectively, the results support a model in which AR activity increases oxidative stress and mediates the PLC-γ2 phosphorylation and PKC activation, which leads to the p38α MAPK activation, resulting in collagen-induced TXA$_2$ generation, TP activation, and aggregation in platelets (see FIG. 13).

Figure 10C:
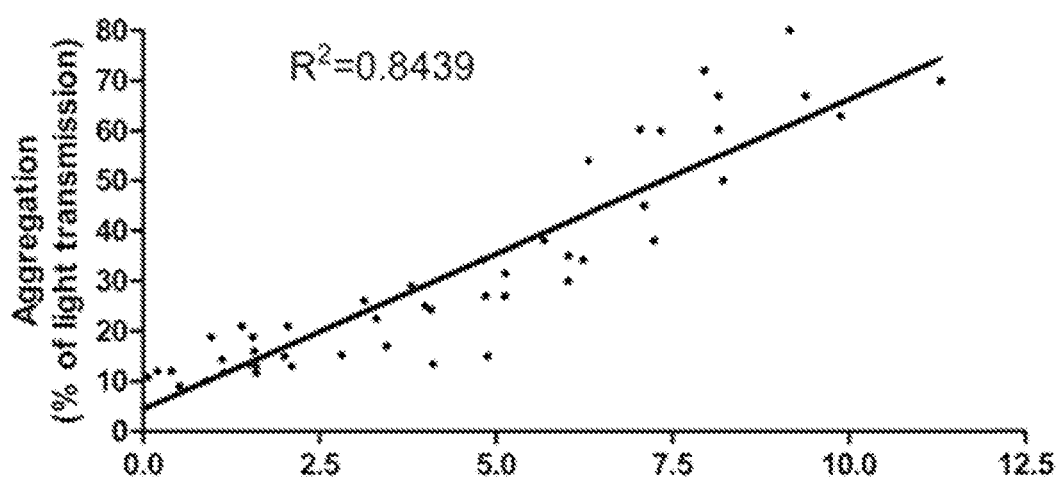

In order to assess the association between TXA$_2$ generation and increased platelet aggregation, the percentage of aggregation was plotted against the level of released TXB$_2$. As shown in FIG. 10C, a linear relationship with positive slope ($R^2$=0.8566, slope=12.11), occurred between TBX$_2$ levels and the percentage of aggregation, indicating that increased platelet aggregation is closely correlated with TXA$_2$ generation in the experimental human models. In addition, this result supports that platelet aggregation increases TXA$_2$ biosynthesis, and increased TXA$_2$ biosynthesis increases platelet aggregation, leading to an amplifying positive feedback mechanism. This important observation provides an explanation for increased platelet activity during hyperglycemia by AR-dependent induction of TXA$_2$ generation.

Example 8

Figure 11:
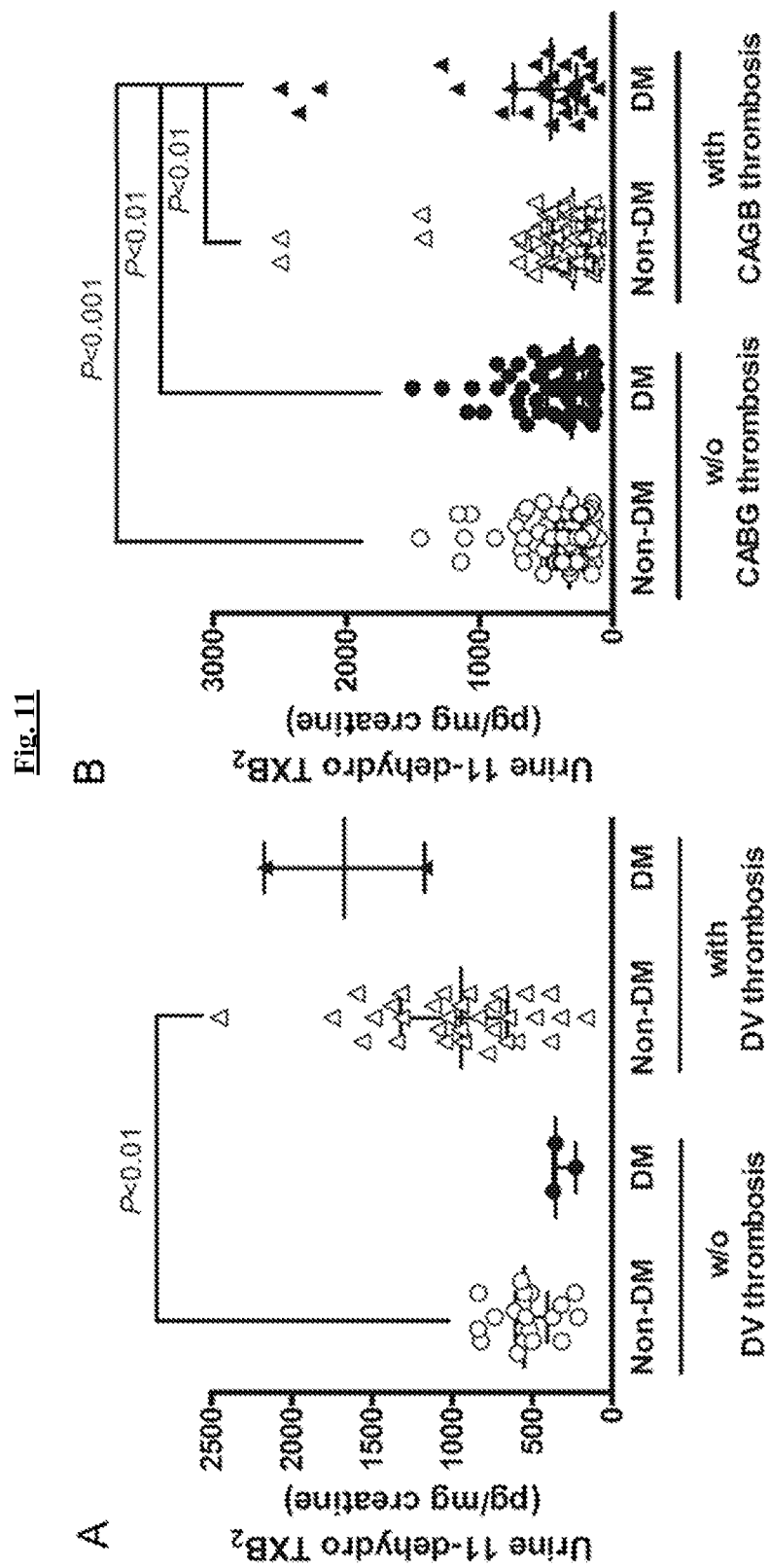
FIG. 11, comprising

Increased Urinary Thromboxane Metabolite (TX-M) Levels in Patients with Deep Venous Thrombosis As shown herein, TXA$_2$ generation is increased with collagen-induced activation of normal human platelets ex vivo, and acute hyperglycemia further enhanced TXA$_2$ biosynthesis in vitro. To determine whether glucose levels and collagen-dependent thrombosis induce TXA$_2$ production in patients, urinary levels of TX-M was measured in a case controlled study of patients with or without deep vein thrombosis (DVT). DVT is known to be caused in part by endothelial damage and collagen exposure. The DVT patients (n=34) and controls (n=23) were characterized by comparable age, cardiovascular risk factors (cigarette smoking, diabetes, hypertensive status, lipid levels), body mass index (BMI) and systemic inflammatory status index (i.e. CRP and fibrinogen). As shown in FIG. 11A, there was a statistically significant increase of TX-M in the DVT patients vs. controls (For Non DM patients without DVT, the median and IQR (Q1-Q3) was 551.5 pg/mL creatinine (436.2 to 600); For Non DM patients with DVT, 942 pg/mL creatinine, (657.5 to 1319)). Interestingly, the few diabetic patients that were present had very high TX-M only in the presence of DVT. A further study was necessary in a patient population with a higher incidence of diabetes mellitus to assess the link between diabetes mellitus (hyperglycemia), thrombosis (platelet hyperactivity) and TXA$_2$ generation in vivo (urinary levels of TX-M).

Example 9

Increased Urinary Levels of TX-M in Diabetic Patients with Saphenous Vein Coronary Artery Bypass Graft Thrombosis Treated with Aspirin Based upon the interesting DVT findings, another case controlled study was performed, assessing another patient population with a much higher prevalence of diabetes mellitus: a severe coronary artery disease population with coronary artery bypass graft (CABG) thrombosis (Table 1). Not surprisingly, with such severe disease, all patients were on aspirin (to inhibit platelet COX-1-dependent production of TXA$_2$) for secondary prevention of further cardiovascular events. The groups were comparable for age and cardiovascular risk factors. As shown in FIG. 11B, patients without graft occlusion exhibited no TX-M differences between diabetics and non-diabetics while on aspirin (For Non DM without CABG thrombosis, the median and IQR (Q1-Q3) was 328 pg/mL creatinine (233 to 424.5); For DM without CABG thrombosis, 312 pg/mL creatinine, (226 and 495)). However, amongst those with thrombosis, there was a significant difference between diabetics and non-diabetics (For Non DM with CABG thrombosis, the median and IQR (Q1-Q3) was 304 pg/mL creatinine (206 and 450); For DM with CABG thrombosis, 466.5 pg/mL creatinine (275 and 718). This supports the experimental observation that $TXA_2$ biosynthesis in vivo is enhanced in patients with both thrombosis and diabetes mellitus despite the use of aspirin. The mechanism for this apparent insensitivity to aspirin in the presence of thrombosis and diabetes required further exploration.

TABLE 1

Cardiovascular Risk Factors for the Populations Studied

|  | DVT Study | RIGOR Study |
|---|---|---|
| N | 57 | 291 |
| Male/Female | 17/40 | 230/61 |
| Median Age (Range) | 62.5 (33-82) | 63 (55-72) |
| BMI | 29.2 (±5.7) | 29.5 (±6.13) |
| Dyslipidemia | 34 (50.0%) | 191 (83.4%) |
| Diabetes | 8 (11.8%) | 84 (36.7%) |
| Hypertension | 35 (51.5%) | 187 (81.7%) |
| Smokers | 10 (14.7%) | 52 (22.7%) |

Example 10

Aspirin Ex Vivo does not Cause a Complete Saturation of Platelet COX-1 Activity

In order to verify whether enhanced generation of $TXA_2$ in vivo was a consequence of inadequate inhibition of platelet COX-1 (ex vivo) by aspirin administration, residual generation of $TXB_2$ was compared 12 h after the last dose of aspirin, in whole blood allowed to clot for 1 h at 37° C. (serum $TXB_2$) which is an index of maximal capacity of platelets to generate $TXB_2$.

Figure 12:
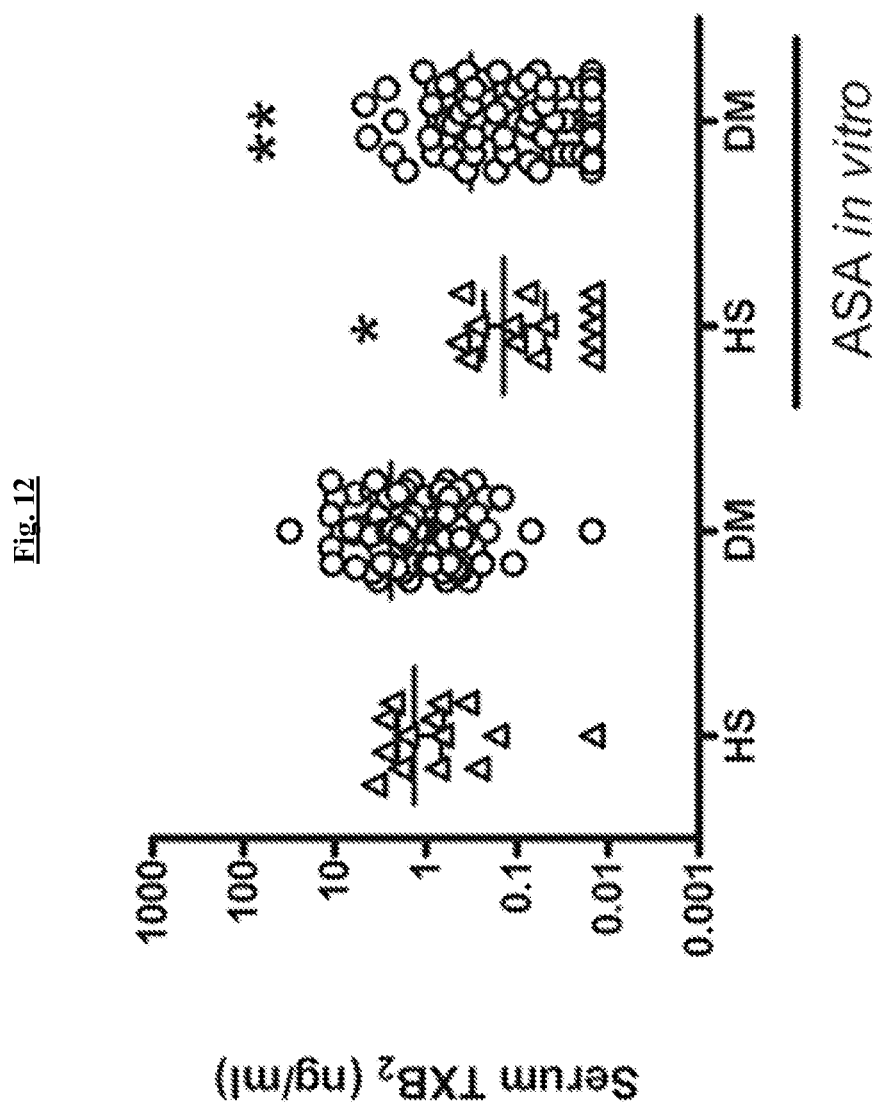
FIG. 12 is a graph illustrating the effect of in vitro administration of Aspirin on the residual $TXB_2$ generation in healthy subjects (HS) and diabetic (DM) patients with severe cardiovascular diseases. The serum $TXB_2$ level, marker of platelet COX-1 activity, was assessed in HS (n=14) and DM (n=102) patients with low dose aspirin (100 mg/day). The residual generation of $TXB_2$ was assessed in whole blood allowed to clot for 1 h at 37° C., 12 h after the last dose of aspirin. Data are expressed as median with interquartile range. **P<0.01 & *P<0.05 compared with values in the corresponding group without ASA in vitro.

Enhanced median values of residual generation of platelet $TXB_2$ were detected in diabetic patients versus healthy subjects; however, the differences were not statistically significant. However, 12% of diabetic patients had higher values of residual $TXB_2$ (i.e., 4 ng/mL) than the upper extreme value of serum $TXB_2$ detected in control subjects after aspirin administration. In order to verify whether in these patients higher generation of platelet $TXB_2$ was due to the phenomenon of aspirin resistance which implies that the aspirin target, i.e., COX-1, is less sensitive to inactivation by aspirin, residual generation of $TXB_2$ was assessed after adding aspirin (50 μg/mL) in vitro. As shown in FIG. 12, in vitro aspirin caused a further significant reduction of $TXB_2$ generation both in diabetic patients and healthy subjects. Importantly, only 2% of patients had residual $TXB_2$ levels higher than 4 ng/mL in diabetic groups with aspirin in vitro. The results show that in almost all patients with diabetes and cardiovascular disease, aspirin is able to reduce serum $TXB_2$ both ex vivo and in vitro to an similar extent. Thus the apparent aspirin insensitivity is not due to aspirin resistance. It is important to point out that the observed residual COX-1 activity is present even after aspirin treatment. This COX-1 activity likely converts the increased AA substrate generated from the p38α MAPK/$PLA_2$ activation pathway leading to enhanced platelet $TXA_2$ generation and increased platelet activation under conditions of acute hyperglycemia and collagen activation.

Example 11

Analysis of Human Thromboxane Receptor (hTP) Genetic Variants in Cardiovascular Patients In order to ensure and confirm that the increase in thromboxane levels was not secondary to a dysfunctional or defective thromboxane receptor, genomic DNA from patients and volunteers from the Yale, Chieti and Johns Hopkins studies was sequenced for variants in the thromboxane receptor gene (TBXA2R). No dysfunctional nonsynonomous mutations could account for the observed results (data not shown). This result demonstrates that the difference in TX-M level between the diabetic and non-diabetic patients could not be attributed to structural defects in the hTP.

Example 12

Platelet Aggregation

Figure 17:
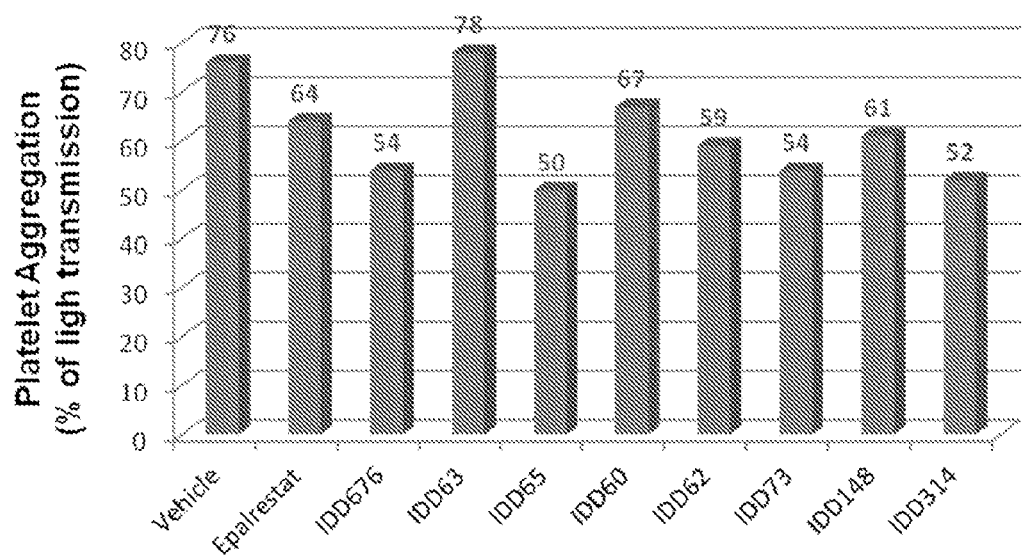
FIG. 17 is a bar graph illustrating platelet aggregometry studies with various aldose reductase inhibitors.
Figure 18:
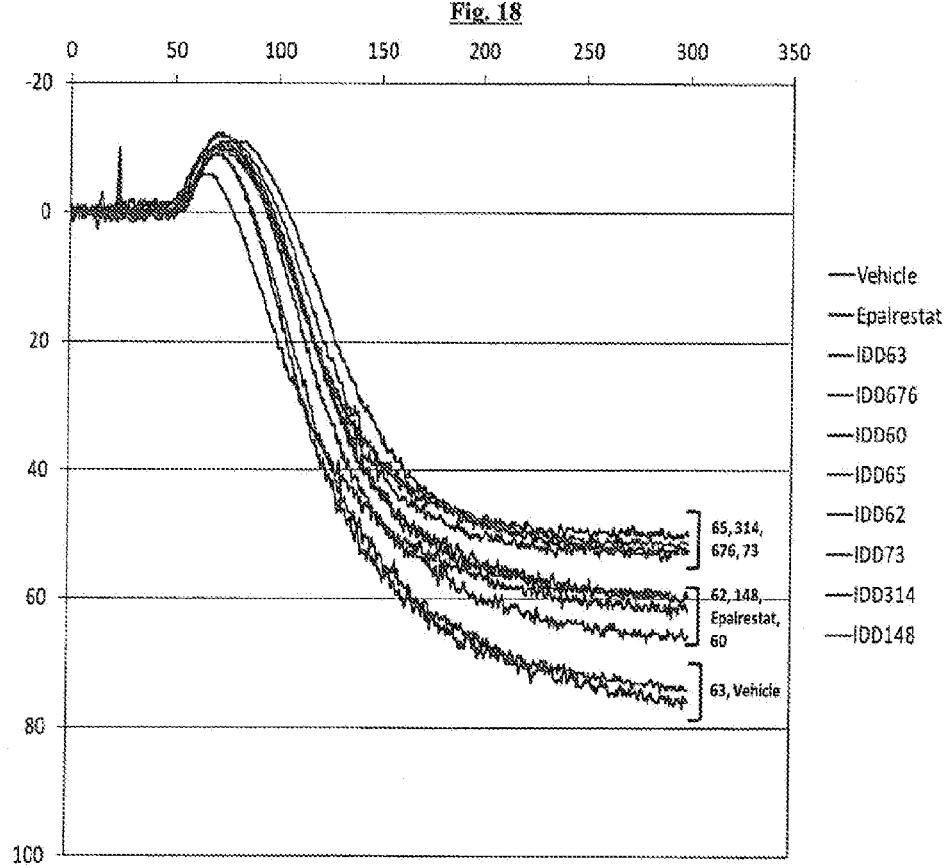
FIG. 18 is a graph illustrating tracings corresponding to the experiments illustrated in FIG. 17.

Washed platelet ($1\times10^8$) were incubated with AR inhibitors for 1 hour at 37° C. For aggregometry studies, 0.5 μL of collagen solution (with a final concentration of 1 μg/mL) was added into 500 μL of washed platelet, and then the light transmission was measured for 5 min. For all the tested AR inhibitors, the concentration used was 10 μM (which was higher than the respective $IC_{50}$ values). The percentage of platelet aggregation, as measured in terms of light transmission, is summarized in FIG. 17, and representative tracings are depicted in FIG. 18. Aggregometry results are summarized in Table 2.

TABLE 2

Aldose Reductase Inhibitor Results

| Compound number | Compound name | % reduction | $IC_{50}$'s |
|---|---|---|---|
| IDD 676 | Lidorestat | 54% | 5 nM |
| IDD 63 | Tolrestat | 78% | 12 nM |
| IDD 65 | Zopolrestat | 50% | 9 nM |
| IDD 60 | Sorbinil | 67% | 1300 nM |
| IDD 62 | Minalrestat | 59% | 11 nM |
| IDD 73 | Risarestat (CT-112) | 54% | 294 nM |
| IDD 148 | Zenarestat | 61% | 8 nM |
| IDD 314 | NZ 314 | 52% | 718 nM |

Example 13

Figure 13:
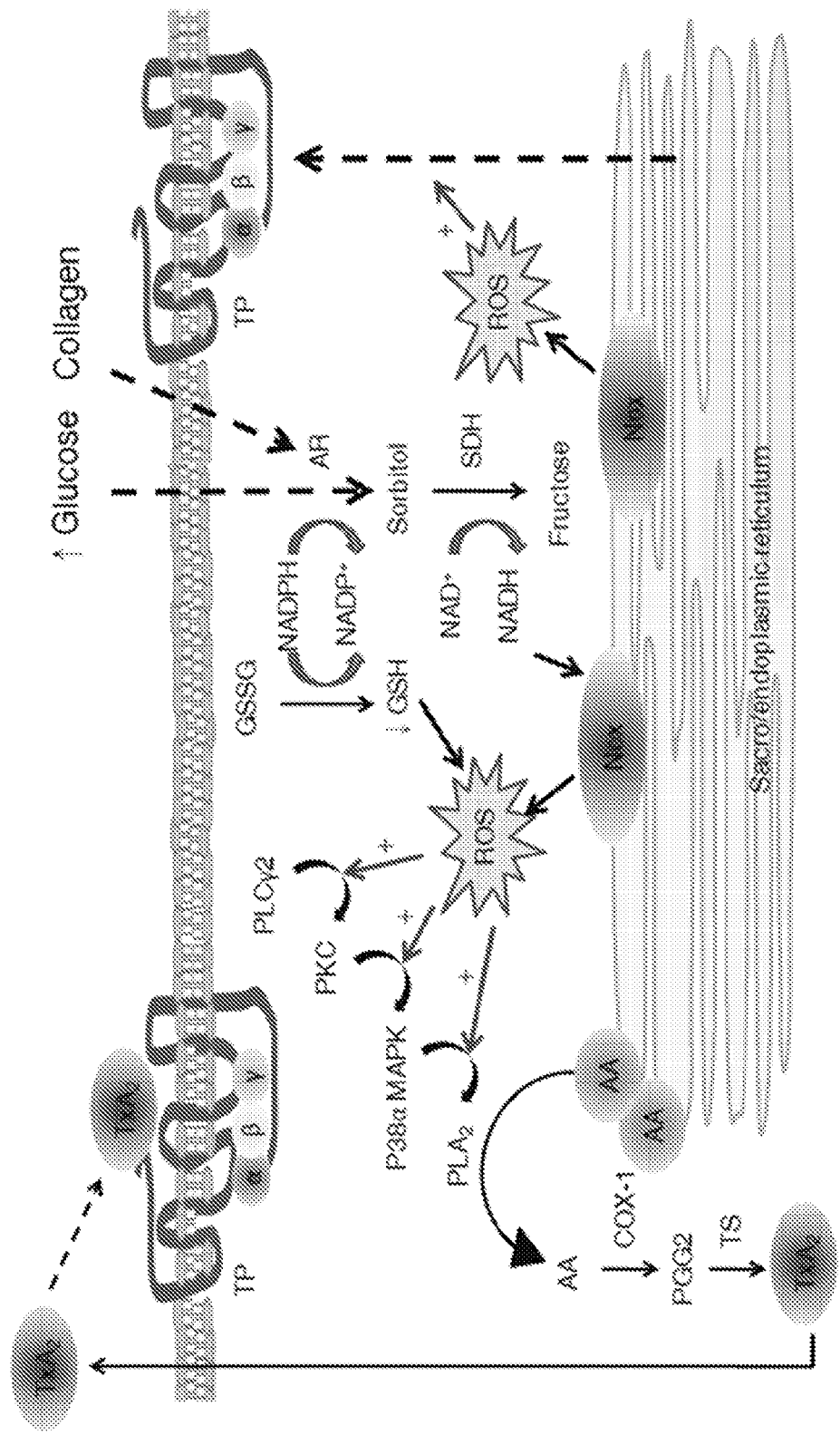
FIG. 13 is a scheme illustrating a non-limiting proposed mechanism for hyperglycemia-induced platelet hyperactivity through thromboxane signaling mediated by AR pathway.

The mechanism leading to thromboxane release and platelet hyperactivity in diabetes mellitus was herein investigated. The present studies demonstrate for the first time that AR plays a central role in synergistically transducing hyperglycemia and collagen exposure to thromboxane release, increased cell surface thromboxane receptor expression, and enhanced platelet activity. This effect is associated with reactive oxygen species generation and the activation of PLC-γ2, PKC βII & δ, and p38α MAPK (FIG. 13). The clinical studies supported these results as increased $TXA_2$ generation in vivo, particularly in diabetic patients, reflected underlying thrombovascular disease (deep venous thrombosis and coronary artery bypass graft thrombosis). These mechanistic insights may explain in part the poor prognosis observed with patients presenting with hyperglycemia and acute coronary syndrome. Enhanced platelet activity due to a combination of hyperglycemia and collagen exposure may predispose to further thromboembolic disease.

Complex Regulatory Pathway Required for the Synergistic Effects of Glucose on Collagen Stimulated Aggregation The role and relationship of the AR pathway to thromboxane release and platelet hyperactivity has been unexplored. The studies described herein demonstrate that AR plays a critical role in transducing collagen signaling in platelet aggregation and this is further enhanced in conditions of hyperglycemia. Further, the studies here described demonstrated that PLC-γ2 phosphorylation is greatly increased in the glucose-treated platelets and collagen-induced platelet aggregation, and PLC inhibition using U73122 effectively prevented the collagen-induced $TXB_2$ generation and aggregation, suggesting that PLC-γ2 phosphorylation is required for the collagen-induced platelet aggregation. Looking further downstream (FIG. 13), in high glucose and collagen-stimulated platelets, PKC-α, βII and δ were translocated from cytosol to membrane with concomitant increase in their phosphorylated forms, thus supporting a role of PKC-α, βII and δ in this process. Thus a complex web of signaling components is involved in platelet activation upon exposure to collagen and hyperglycemia (FIG. 13). The studies described herein unify many of the platelet-dependent signaling components in the AR transduction of glucose signaling. AR appears to serve as a master switch for collagen induced platelet aggregation being enhanced by the presence of high glucose.

Oxidative Stress Plays an Important Role in Thromboxane Induced Platelet Hyperactivity Glucose flux through AR generates oxidative stress by mechanisms such as NADPH depletion, decreasing GSH levels (NADPH is the co-factor for glutathione reductase that regenerate GSH from GSSH) and increasing advanced glycation end products, generating ROS (Chung & Chung, 2005, Curr. Drug Targets 6:475-48). Also, $TXA_2$ biosynthesis is upregulated by oxidant formation (for example, hydrogen peroxide) during platelet aggregation (Caccese et al., 2000, Thromb. Haemost. 83:485-490; Leo et al., 1997, Circul. 95:885-891; Wachowicz et al., 2002, Platelets 13:175-182). Here, the studies reported show that this potentiates p38 MAPK/cPLA$_2$, signaling, which catalyzes arachidonic acid release, producing $TXA_2$. Interestingly, reactive oxygen species (ROS) derived from platelet activation also play an important role in signaling upon collagen-induced platelet aggregation. Free radical species act as secondary messengers that increase cytosolic $Ca^{2+}$ during the initial phase of platelet activation processes, and PKC is involved in receptor-mediated ROS production in platelets (Wachowicz et al., 2002, Platelets 13:175-182). Previous studies also showed that ROS formation is involved in collagen-induced platelet aggregation, which is dependent on arachidonic acid release and its metabolism (Caccese et al., 2000, Thromb. Haemost. 83:485-490), thus ROS may be needed for platelet activation (Iuliano et al., 1997, Free Radic. Biol. Med. 22:999-1006; Pignatelli et al., 1999, Arterioscler. Thromb. Vasc. Biol. 19:2542-2547). Indeed, our studies demonstrate that oxidative stress is significantly increased in collagen-stimulated platelets, and inhibition of AR partly attenuated the collagen-induced oxidative stress, supporting an important role for AR exacerbated oxidative stress, in collagen-dependent signaling. Furthermore, the studies have now demonstrated oxidative stress-induced stabilization and relocation of the TX receptor to the cell surface (Wilson et al., 2009, J. Lipid Res. 50:1047-1056; Ball et al., PLoS One 5:e12798).

A Positive Feedback Cycle of Thromboxane Release and Platelet Hyperactivity

Urinary TX-M, reflecting the whole biosynthesis of $TXA_2$ in the body, mainly by platelets with a minor contribution from extraplatelet sources, is significantly higher in diabetes, with the absolute post-aspirin values in diabetics being comparable to non-aspirinated controls (Davi et al., 1990, N. Engl. J. Med. 322:1769-1774; Ferroni et al., 2004, J. Thromb. Haemost. 2:1282-1291). In fact, the present studies indicated that platelet degranulation and synthesis of $TXA_2$ mediates further platelet activation in DM.

As illustrated in FIG. 19, experiments performed with platelets from a diabetic patient indicated that addition of aldose reductase reduced in vitro aggregation of these platelets. Further, the experiments performed indicated that addition of aldose reductase reduced in vitro expression of TX-M (thromboxane B2) induced by exposure of these platelets to collagen.

The studies described herein further addressed the question as to the initiating events that lead to this cascade of hyperactivation, thrombosis and hyperactivation. As described, it may be that the trigger is endothelial damage (collagen exposure) and when combined with hyperglycemia induced oxidative stress, reactive oxygen species initiates an amplifying cycle of increased PLC/PKC/p38 MAPK signaling, $TXA_2$ generation and platelet hyperactivation.

Aldose Reductase Inhibitors as Antiplatelet Therapy

The study highlights the importance of concurrent clinical studies to substantiate in vitro findings. Diabetic patients with high urinary levels of TX-M despite aspirin treatment may have underlying occult endothelial damage and thrombovascular disease. In the context of vascular damage with collagen exposure and HG, unacetylated platelet COX-1 despite aspirin, may participate in $TXA_2$ biosynthesis, on a background of increased p38 MAPK induced PLA$_2$ activity and thus enhanced AA substrate. Higher doses of aspirin or low-dose aspirin given twice daily may translate into an appropriate suppression of $TXA_2$ in vivo (assessing the levels of urinary TX-M). Alternatively the addition of AR inhibitors should be considered to mitigate enhanced $TXA_2$ generation despite aspirin treatment in patients with diabetes. Epalrestat used in the present study is an aldose reductase inhibitor that is approved in Japan to prevent or slow the progression of diabetic neuropathy (Ramirez & Borja, 2008, Pharmacother. 28:646-655; Hotta et al., 1996, J. Diab. Compl. 10:168-172; Hotta et al., 2006, Diab. Care 29:1538-1544). The reported study using human platelets demonstrated that the hyperglycemia-induced thromboxane signaling and hyperaggregability was effectively attenuated by treatment with epalrestat. The use of ARIs may be particularly effective against postprandial hyperglycemia, which is associated with enhanced lipid peroxidation and platelet activation in early type 2 diabetes mellitus (Santilli et al., 2010, J. Thromb. Haemost. 8:828-837), and increased platelet aggregation in diabetic patients with microangiopathy (Kajita et al., 2001, Platelets 12:343-351). The addition of ARI may be a new therapeutic option to prevent thrombotic events in diabetic patients.

The studies described herein support the assertion that enhanced platelet activity associated with diabetes mellitus may be both a cause (thrombosis from, for example, plaque rupture) and a consequence (metabolic disturbance) of disease. The combination of hyperglycemia during collagen activation leads to a positive feedback cycle of release of platelet thromboxane and enhanced platelet aggregation (cause and consequence). Moreover, aldose reductase leading to enhanced ROS production and thromboxane generation plays a major role in this synergistic response. The findings disclosed herein support the use of higher doses of aspirin, however inhibition of vascular prostacyclin biosynthesis makes this choice inadvisable. The foundation for antiplatelet therapy in diabetic patients may very well be a combination of aspirin with AR inhibitors (and/or thromboxane inhibitors) for both primary and secondary prevention of cardiovascular events.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating or ameliorating a condition selected from the group consisting of platelet hyperactivity and abnormal thrombus formation in a subject in need thereof, wherein the subject has an elevated level of 11-dehydro-thromboxane $B_2$ (TX-M) as compared to a normal subject,
the method comprising administering to the subject with an elevated level of TX-M as compared to a normal subject a therapeutically effective amount of at least one aldose reductase inhibitor,
the method further comprising administering to the subject aspirin or a salt thereof,
wherein the aldose reductase inhibitor is selected from the group consisting of tolrestat, epalrestat, ranirestat, fidarestat, lidorestat, zopolrestat, sorbinil, minalrestat, risarestat, zenarestat, NZ-314, a salt thereof, and any combinations thereof,
wherein administration of the at least one aldose reductase inhibitor and the aspirin treats or ameliorates the condition in the subject.

2. The method of claim 1, wherein the subject is diabetic or has increased cardiovascular risk.

3. The method of claim 2, wherein the subject has been diagnosed with cerebrovascular disease, peripheral vascular disease or coronary artery disease.

4. The method of claim 1, wherein the pharmaceutical composition and the aspirin are co-administered to the subject.

5. The method of claim 4, wherein the pharmaceutical composition and the aspirin are co-formulated and co-administered to the subject.

6. The method of claim 1, wherein administering aspirin or a salt thereof to the subject in the absence of at least one aldose reductase inhibitor does not treat or ameliorate the condition in the subject.

7. The method of claim 1, wherein the elevated level of TX-M in the subject is at least 50% higher than the average level of TX-M in a normal subject.

8. The method of claim 1, wherein administering of aspirin or a salt thereof in the absence of at least one aldose reductase inhibitor to the subject has no or minimal effect on the elevated level of TX-M in the subject.

9. The method of claim 1, wherein the subject is a mammal.

10. The method of claim 9, wherein the mammal is human.

11. The method of claim 1, wherein the pharmaceutical composition is administered to the subject by an administration route selected from the group consisting of inhalational, oral, rectal, vaginal, parenteral, topical, transdermal, pulmonary, intranasal, buccal, ophthalmic, intrathecal, and any combinations thereof.

* * * * *